US010991984B2

(12) United States Patent
Itakura et al.

(10) Patent No.: US 10,991,984 B2
(45) Date of Patent: Apr. 27, 2021

(54) IONIC LIQUID, NONAQUEOUS ELECTROLYTE, AND POWER STORAGE DEVICE

(71) Applicant: SEMICONDUCTOR ENERGY LABORATORY CO., LTD., Atsugi (JP)

(72) Inventors: Toru Itakura, Kanagawa (JP); Kyosuke Ito, Saitama (JP); Rie Yokoi, Kanagawa (JP); Jun Ishikawa, Kanagwa (JP)

(73) Assignee: Semiconductor Energy Laboratory Co., Ltd., Kanagawa-ken (JP)

( * ) Notice: Subject to any disclaimer, the term of this patent is extended or adjusted under 35 U.S.C. 154(b) by 0 days.

(21) Appl. No.: 15/008,487

(22) Filed: Jan. 28, 2016

(65) Prior Publication Data

US 2016/0141719 A1    May 19, 2016

Related U.S. Application Data

(63) Continuation of application No. 13/719,542, filed on Dec. 19, 2012, now Pat. No. 9,252,459.

(30) Foreign Application Priority Data

Dec. 23, 2011  (JP) .............................. JP2011-282486

(51) Int. Cl.
*H01M 10/0569* (2010.01)
*H01M 10/0568* (2010.01)
(Continued)

(52) U.S. Cl.
CPC ..... *H01M 10/0569* (2013.01); *H01M 10/052* (2013.01); *H01M 10/0568* (2013.01);
(Continued)

(58) Field of Classification Search
CPC ... C07C 275/06; C07C 275/02; C07C 233/05; C25D 3/44; C25D 3/665; H01M 10/052;
(Continued)

(56) References Cited

U.S. PATENT DOCUMENTS

| 5,011,934 A * | 4/1991 | Schulte ................ C07D 231/12 548/335.1 |
| 6,284,852 B1 | 9/2001 | Lynn et al. |

(Continued)

FOREIGN PATENT DOCUMENTS

| CN | 001802362 A | 7/2006 |
| CN | 101784524 A | 7/2010 |

(Continued)

OTHER PUBLICATIONS

Machine English language translation—Sakabe Hikari et al. JP 2003331918 (A)—Nov. 21, 2003 "Cold melting salt, and lithium secondary cell using the same" (Year: 2003).*

(Continued)

*Primary Examiner* — Jonathan G Jelsma
*Assistant Examiner* — Omar M Kekia
(74) *Attorney, Agent, or Firm* — Nixon Peabody LLP; Jeffrey L. Costellia

(57) ABSTRACT

A nonaqueous electrolyte of the present invention includes an ionic liquid including a first alicyclic quaternary ammonium cation having one or more substituents, a second alicyclic quaternary ammonium cation having an alicyclic skeleton that is the same as an alicyclic skeleton of the first alicyclic quaternary ammonium cation, and a counter anion to the first alicyclic quaternary ammonium cation and the second alicyclic quaternary ammonium cation and an alkali metal salt. In the second alicyclic quaternary ammonium cation, one of substituents bonded to a nitrogen atom in the alicyclic skeleton is a substituent including a halogen ele- (Continued)

ment. In the ionic liquid, the amount of a salt including the second alicyclic quaternary ammonium cation is less than or equal to 1 wt % per unit weight of the ionic liquid, or is less than or equal to 0.8 wt % per unit weight of the nonaqueous electrolyte.

22 Claims, 14 Drawing Sheets

(51) Int. Cl.
*H01M 10/052* (2010.01)
*C25D 3/44* (2006.01)
*C07C 275/02* (2006.01)
*C07C 275/06* (2006.01)
*C25D 3/66* (2006.01)
*C07C 233/05* (2006.01)

(52) U.S. Cl.
CPC .......... *C07C 233/05* (2013.01); *C07C 275/02* (2013.01); *C07C 275/06* (2013.01); *C25D 3/44* (2013.01); *C25D 3/665* (2013.01); *H01M 2300/0045* (2013.01); *Y02E 60/10* (2013.01)

(58) Field of Classification Search
CPC ..... H01M 10/0569; H01M 2300/0045; H01M 10/0568; Y02E 60/122
USPC .......................................................... 429/199
See application file for complete search history.

(56) References Cited

U.S. PATENT DOCUMENTS

| | | | |
|---|---|---|---|
| 6,486,279 B2 | 11/2002 | Lynn et al. | |
| 6,853,472 B2 | 2/2005 | Warner et al. | |
| 6,961,168 B2 | 11/2005 | Agrawal et al. | |
| 7,026,510 B2 | 4/2006 | Allegretti et al. | |
| 7,119,937 B2 | 10/2006 | Warner et al. | |
| 7,297,289 B2 | 11/2007 | Sato et al. | |
| 7,450,292 B1 | 11/2008 | Burrell et al. | |
| 7,471,502 B2 | 12/2008 | Sato et al. | |
| 7,605,271 B2 | 10/2009 | Uchimura et al. | |
| 7,633,669 B2 | 12/2009 | Burrell et al. | |
| 7,763,186 B2 | 7/2010 | Burrell et al. | |
| 7,834,197 B2 | 11/2010 | Nishida et al. | |
| 8,088,917 B2 | 1/2012 | Forsyth et al. | |
| 8,366,956 B2 | 2/2013 | Nishida et al. | |
| 8,507,132 B2 | 8/2013 | Wakita et al. | |
| 8,686,134 B2 | 4/2014 | Forsyth et al. | |
| 8,747,690 B2 | 6/2014 | Nishida et al. | |
| 8,795,544 B2 | 8/2014 | Ito et al. | |
| 2004/0204611 A1* | 10/2004 | Lappe .................... | C07C 209/28 564/471 |
| 2005/0005840 A1* | 1/2005 | Bonrath ............... | C07D 231/12 117/2 |
| 2007/0042271 A1 | 2/2007 | Nishida et al. | |
| 2007/0099079 A1 | 5/2007 | Matsumoto et al. | |
| 2007/0099090 A1 | 5/2007 | Oh et al. | |
| 2007/0194275 A1* | 8/2007 | Masuda ................. | C08F 291/00 252/182.24 |
| 2008/0251759 A1* | 10/2008 | Kalb ....................... | C07C 211/62 252/183.13 |
| 2008/0296531 A1 | 12/2008 | Whiston et al. | |
| 2009/0312579 A1* | 12/2009 | Kubanek ................ | B01J 23/002 564/473 |
| 2010/0178555 A1 | 7/2010 | Best | |
| 2010/0209784 A1 | 8/2010 | Yamazaki et al. | |
| 2010/0227228 A1 | 9/2010 | Yamazaki et al. | |
| 2010/0286152 A1 | 11/2010 | Bernasconi et al. | |
| 2010/0298377 A1 | 11/2010 | Aletru et al. | |
| 2011/0020706 A1 | 1/2011 | Nesper | |
| 2011/0070486 A1 | 3/2011 | Matsumoto et al. | |
| 2011/0294005 A1 | 12/2011 | Kuriki et al. | |
| 2012/0002349 A1 | 1/2012 | Ito et al. | |
| 2012/0021279 A1 | 1/2012 | Le Bideau et al. | |
| 2012/0045692 A1 | 2/2012 | Takemura et al. | |
| 2012/0088151 A1 | 4/2012 | Yamazaki et al. | |
| 2012/0088156 A1 | 4/2012 | Nomoto et al. | |
| 2012/0308882 A1 | 12/2012 | Ito et al. | |
| 2012/0328960 A1 | 12/2012 | Ito et al. | |
| 2013/0164609 A1 | 6/2013 | Ito et al. | |
| 2014/0342245 A1 | 11/2014 | Ito et al. | |

FOREIGN PATENT DOCUMENTS

| | | | |
|---|---|---|---|
| CN | 101821892 A | 9/2010 | |
| CN | 102142316 A | 8/2011 | |
| CN | 102332609 A | 1/2012 | |
| EP | 1380569 A | 1/2004 | |
| EP | 1642894 A | 4/2006 | |
| EP | 1707265 A | 10/2006 | |
| EP | 2090565 A | 8/2009 | |
| EP | 2135859 A | 12/2009 | |
| EP | 2172463 A | 4/2010 | |
| EP | 2295399 A | 3/2011 | |
| JP | 2002-516911 | 6/2002 | |
| JP | 2003-331918 A | 11/2003 | |
| JP | 2003331918 | * 11/2003 | ............ H01M 10/05 |
| JP | 2005-504121 | 2/2005 | |
| JP | 2005-225843 A | 8/2005 | |
| JP | 2005-251510 A | 9/2005 | |
| JP | 2006-278167 A | 10/2006 | |
| JP | 2007-039460 A | 2/2007 | |
| JP | 2007-141489 A | 6/2007 | |
| JP | 2008-084664 A | 4/2008 | |
| JP | 2009-138254 A | 6/2009 | |
| JP | 2010-529033 | 8/2010 | |
| JP | 2010-530402 | 9/2010 | |
| JP | 2011-521888 | 7/2011 | |
| JP | 2011-192963 A | 9/2011 | |
| WO | WO-1999/022865 | 5/1999 | |
| WO | WO-2003/029187 | 4/2003 | |
| WO | WO-2004/001877 | 12/2003 | |
| WO | WO-2005/026827 | 3/2005 | |
| WO | WO-2008/140496 | 11/2008 | |
| WO | WO-2008/148853 | 12/2008 | |
| WO | WO-2008/150842 | 12/2008 | |
| WO | WO-2009/003224 | 1/2009 | |

OTHER PUBLICATIONS

Sakaebe.H et al., "N-Methyl-N-propylpiperidinium bis(trifluoromethanesulfonyl)imide (PP13-TFSI)—novel electrolyte base for Li battery", Electrochemistry Communications, Jul. 1, 2003. vol. 5, No. 7, pp. 594-598.

Matsumoto.H et al., "Fast cycling of Li/LiCoO2 cell with low-viscosity ionic liquids based on bis(fluorosulfonyl)imide [FSI]", Journal of Power Sources, Mar. 22, 2006, vol. 160, No. 2, pp. 1308-1313.

MacFarlane.D et al., "Pyrrolidinium Imides: A New Family of Molten Salts and Conductive Plastic Crystal Phases", J. Phys. Chem. B (Journal of Physical Chemistry B), Feb. 2, 1999, vol. 103, No. 20, pp. 4164-4170.

Chinese Office Action (Application No. 201210563647.6) dated Sep. 1, 2015.

Belhocine.T et al., "New ionic liquids from azepane and 3-methylpiperidine exhibiting wide electrochemical windows", Green Chemistry, Nov. 30, 2010, vol. 13, No. 1, pp. 59-63, The Royal Society of Chemistry.

Nockemann.P et al., "Purification of imidazolium ionic liquids for spectroscopic applications", Chem. Phys. Lett. (Chemical Physics Letters), Sep. 23, 2005, vol. 415, No. 1-3, pp. 131-136.

Burrell.A et al., "The large scale synthesis of pure imidazolium and pyrrolidinium ionic liquids", Green Chemistry, 2007, vol. 9, No. 5, pp. 449-454.

(56) References Cited

OTHER PUBLICATIONS

Cassol. C et al., "A Simple and Practical Method for the Preparation and Purity Determination of Halide-Free Imidazolium Ionic Liquids", Advanced Synthesis & Catalysis, Jan. 19, 2006, vol. 348, No. 1-2, pp. 243-248.

* cited by examiner 218  217

218  217

IONIC LIQUID, NONAQUEOUS ELECTROLYTE, AND POWER STORAGE DEVICE

BACKGROUND OF THE INVENTION

1. Field of the Invention

The present invention relates to a power storage device including an ionic liquid (also referred to as room temperature molten salt).

Note that the power storage device indicates all elements and devices which have a function of storing power.

2. Description of the Related Art

A lithium secondary battery which is one of power storage devices is used in a variety of applications including mobile phones, electric vehicles (EV), and the like. Characteristics such as high energy density, excellent cycle characteristics, safety under a variety of operating environments, and the like are necessary for the lithium secondary battery.

Many of the widely used lithium secondary batteries include a nonaqueous electrolyte (also referred to as "nonaqueous electrolyte solution") including a nonaqueous solvent and a lithium salt containing lithium ions. An organic solvent which is often used for the nonaqueous electrolyte is an organic solvent which is liquid at ordinary temperatures and pressures, such as ethylene carbonate which has high dielectric constant and excellent ion conductivity.

However, the organic solvent has volatility and a low flash point. For this reason, in the case where a nonaqueous solvent including the organic solvent is used for an electrolyte solution of a lithium secondary battery, the temperature inside the lithium secondary battery might rise due to a short circuit, overcharge, or the like and the lithium secondary battery might burst or catch fire.

In view of the above, the use of an ionic liquid which has non-flammability and non-volatility as a nonaqueous solvent for a nonaqueous electrolyte of a lithium secondary battery has been proposed.

In the case where the ionic liquid is used for a solvent for the nonaqueous electrolyte of the lithium secondary battery, there is a problem in that a low potential negative electrode material cannot be used because of low reduction resistance of the ionic liquid. Thus, a technique has been disclosed, which enables dissolution and precipitation of lithium which is the low potential negative electrode material without the use of an additive by increasing the reduction resistance of an ionic liquid including a quaternary ammonium salt (see Patent Document 1).

REFERENCE

[Patent Document 1] Japanese Published Patent Application No. 2003-331918

SUMMARY OF THE INVENTION

However, the reduction potential of the ionic liquid whose reduction resistance is thus increased is substantially equivalent to an oxidation-reduction potential of lithium. Further improvement is required for the reduction resistance of the ionic liquid.

Further, when an impurity is included in the nonaqueous electrolyte in a power storage device including a positive electrode, a negative electrode, and a separator, the impurity is decomposed by charging and discharging the power storage device, which leads to deterioration in the characteristics of the power storage device, such as a deterioration in cycle characteristics. In particular, the characteristics of the power storage device remarkably deteriorate when an operating environment has high temperature. For this reason, the impurity needs to be reduced in the nonaqueous solvent and a salt included in the nonaqueous electrolyte.

In some cases, the ionic liquid used as the solvent for the nonaqueous electrolyte of the power storage device is formed to unintentionally include a by-product, which is easily decomposed depending on a synthesis method thereof. In particular, in a synthesis method of an ionic liquid including an alicyclic quaternary ammonium cation, when an organic solvent including a halogen element is used as a reaction solvent to synthesize the ionic liquid by introduction of an alkyl group into an alicyclic skeleton with the use of alkyl halide, an alicyclic quaternary ammonium salt in which a substituent including a halogen element is bonded is formed as a by-product in some cases. In the case where an ionic liquid formed by such a synthesis method is used as the solvent for the nonaqueous electrolyte, the by-product might be an impurity which causes deterioration in the characteristics of the power storage device.

The use of such an ionic liquid including the alicyclic quaternary ammonium cation in which the substituent including the halogen element is bonded as the solvent for the nonaqueous electrolyte of the power storage device leads to deterioration in the characteristics of the power storage device, which is not preferable.

Therefore, an object of one embodiment of the present invention is to provide a high-performance power storage device using an ionic liquid as a solvent for a nonaqueous electrolyte. In particular, another object of one embodiment of the present invention is to provide a power storage device in which an ionic liquid including an alicyclic quaternary ammonium cation is used as a solvent for a nonaqueous electrolyte, and deterioration in the characteristics due to decomposition of a by-product of the ionic liquid (an impurity in the power storage device) is suppressed.

In view of the above objects, in one embodiment of the present invention, a high-purity ionic liquid in which a by-product that might be an impurity of the power storage device is reduced is used in a power storage device including a positive electrode, a negative electrode, and a nonaqueous electrolyte including an ionic liquid.

In particular, in the case where an ionic liquid including an alicyclic quaternary ammonium cation is used as a solvent for the nonaqueous electrolyte, the alicyclic quaternary ammonium cation is synthesized without the use of an organic solvent including an halogen element; thus, a high-purity ionic liquid in which a by-product (in particular, an alicyclic quaternary ammonium cation which has a substituent including a halogen element) is reduced can be manufactured.

Moreover, an ionic liquid with increased reduction resistance can be manufactured by introduction of one or more substituents (in particular, an electron donating substituent) into an alicyclic skeleton of the alicyclic quaternary ammonium cation. With the use of the ionic liquid as the solvent for the nonaqueous electrolyte, the power storage device can have high performance.

Therefore, one embodiment of the present invention is a power storage device including a positive electrode, a negative electrode, and a nonaqueous electrolyte. The nonaqueous electrolyte includes an ionic liquid including a first alicyclic quaternary ammonium cation having one or more substituents, a second alicyclic quaternary ammonium cation having an alicyclic skeleton that is the same as an alicyclic skeleton of the first alicyclic quaternary ammonium cation, and a counter anion to the first alicyclic quaternary ammonium cation and the second alicyclic quaternary ammonium cation and an alkali metal salt. In the second alicyclic quaternary ammonium cation, one of substituents bonded to a nitrogen atom in the alicyclic skeleton is a substituent including a halogen element. In the ionic liquid, an amount of a salt including the second alicyclic quaternary ammonium cation is less than or equal to 1 wt % per unit weight of the ionic liquid, or is less than or equal to 0.8 wt % per unit weight of the nonaqueous electrolyte.

In the above, the one or more substituents are bonded to a carbon atom in the alicyclic skeleton of the first alicyclic quaternary ammonium cation and a carbon atom in the alicyclic skeleton of the second alicyclic quaternary ammonium cation. In addition, the substituent including the halogen element is bonded to the nitrogen atom in the second alicyclic quaternary ammonium cation.

Further, in the above, the number of carbon atoms in the alicyclic skeleton of the first alicyclic quaternary ammonium cation is preferably less than or equal to 5.

Specifically, one embodiment of the present invention is a power storage device including a positive electrode, a negative electrode, and a nonaqueous electrolyte. The nonaqueous electrolyte at least includes an ionic liquid including an alicyclic quaternary ammonium cation represented by General Formula (G1), an alicyclic quaternary ammonium cation represented by General Formula (G2), and an anion selected from any of a monovalent imide-based anion, a monovalent methide-based anion, a perfluoroalkyl sulfonic acid anion, tetrafluoroborate, and hexafluorophosphate and an alkali metal salt. In the ionic liquid, an amount of a salt including the alicyclic quaternary ammonium cation represented by General Formula (G2) is less than or equal to 1 wt % per unit weight of the ionic liquid, or is less than or equal to 0.8 wt % per unit weight of the nonaqueous electrolyte.

[Chemical Formula 1]

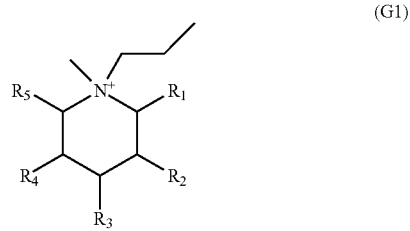

(G1)

(In Chemical Formula 1, $R_1$ to $R_5$ each represent a hydrogen atom or an alkyl group having 1 to 20 carbon atoms.)

[Chemical Formula 2]

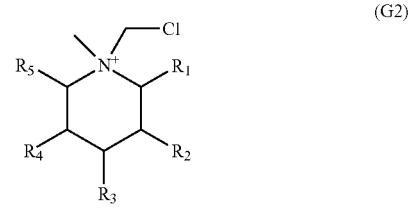

(G2)

(In Chemical Formula 2, $R_1$ to $R_5$ each represent a hydrogen atom or an alkyl group having 1 to 20 carbon atoms.)

Further, in the above, when the alkali metal salt included in the nonaqueous electrolyte is a lithium salt, the power storage device can serve as a power storage device in which carrier ions are lithium ions. Examples of the power storage device include a lithium secondary battery and a lithium ion capacitor.

According to one embodiment of the present invention, a high-performance power storage device using an ionic liquid as a solvent for a nonaqueous electrolyte can be provided. In particular, it is possible to provide a power storage device in which an ionic liquid including an alicyclic quaternary ammonium cation is used as a solvent for a nonaqueous electrolyte, and deterioration in the characteristics due to decomposition of a by-product of the ionic liquid (an impurity in the power storage device) is suppressed. Specifically, a power storage device having high reliability and favorable cycle characteristics in an operating environment at relatively high temperature can be manufactured.

DETAILED DESCRIPTION OF THE INVENTION

Figure 1A:
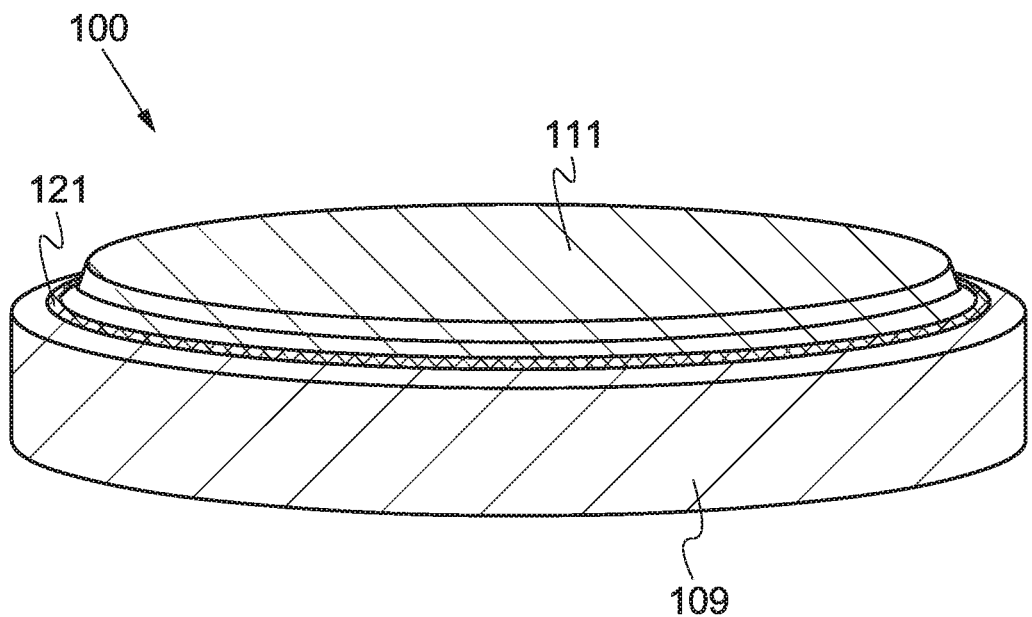
FIGS. 1A and 1B are a perspective view and a cross-sectional view illustrating a structure of a secondary battery of one embodiment of the present invention.

Embodiments of the present invention will be described below in detail with reference to the drawings. However, the present invention is not limited to the following description and it is easily understood by those skilled in the art that the mode and details can be variously changed without departing from the scope and spirit of the present invention. Therefore, the present invention should not be construed as being limited to the description in the following embodiments. In describing structures of the present invention with reference to the drawings, the same reference numerals are used in common for the same portions in different drawings. The same hatching pattern is applied to similar parts, and the similar parts are not especially denoted by reference numerals in some cases. In addition, an insulating layer is not illustrated in a top view in some cases. Note that the size, the layer thickness, or the region of each structure illustrated in each drawing is exaggerated for clarity in some cases. Therefore, the present invention is not necessarily limited to such scales illustrated in the drawings.

Embodiment 1

In this embodiment, a nonaqueous electrolyte used in a power storage device of one embodiment of the present invention is described.

The nonaqueous electrolyte used in the power storage device of one embodiment of the present invention includes an ionic liquid including an alicyclic quaternary ammonium cation and a counter anion to the alicyclic quaternary ammonium cation, which is a solvent, and a salt including carrier ions of the power storage device, which is a solute. The salt is mixed with the solvent at a desired concentration, whereby the nonaqueous electrolyte can be manufactured.

Any salt can be used as the salt including carrier ions of the power storage device as long as it contains alkali metal ions, alkaline earth metal ions, beryllium ions, or magnesium ions. Examples of the alkali metal ion include a lithium ion, a sodium ion, and a potassium ion. Examples of the alkaline earth metal ion include a calcium ion, a strontium ion, and a barium ion. Note that in this embodiment, a lithium salt including lithium ions is used as the salt. Examples of the lithium salt include lithium chloride (LiCl), lithium fluoride (LiF), lithium perchlorate ($LiClO_4$), lithium tetrafluoroborate ($LiBF_4$), $LiAsF_6$, $LiPF_6$, and $Li(CF_3SO_2)_2N$.

The alicyclic quaternary ammonium cation in the ionic liquid has a structure in which two substituents with different structures are bonded to a nitrogen atom and one or more substituents are bonded to a carbon atom in an alicyclic skeleton of the alicyclic quaternary ammonium cation.

In other words, the alicyclic quaternary ammonium cation of the ionic liquid is an alicyclic quaternary ammonium cation having an asymmetrical structure. An example of the substituents bonded to the nitrogen atom is an alkyl group having 1 to 4 carbon atoms. Note that the substituents bonded to the nitrogen atom are not limited thereto and a variety of substituents can be used as long as the alicyclic quaternary ammonium cation has the asymmetrical structure.

As an example of introducing two alkyl groups with different structures into a nitrogen atom, a nitrogen-containing alicyclic compound in which an alkyl group is bonded to a nitrogen atom reacted with alkyl halide in which the number of carbon atoms is different from that of the alkyl group. By the reaction took place in an organic solvent including a halogen element, in addition to the alicyclic quaternary ammonium cation that is a main product, an alicyclic quaternary ammonium cation in which a substituent including the halogen element is bonded to a nitrogen atom is formed as a cation that is a by-product. The by-product has the same alicyclic skeleton as the main product. Because separation and purification of the by-product are difficult, the by-product finally remains as an impurity in a synthesized ionic liquid. When such an ionic liquid including the by-product is used as the solvent for the nonaqueous electrolyte, the by-product becomes an impurity in the power storage device, and the by-product is decomposed by charging and discharging the power storage device, leading to deterioration in the characteristics of the power storage device. In particular, the characteristics of the power storage device remarkably deteriorate when an operating environment has high temperature. Note that in this specification, the main product is referred to as a first alicyclic quaternary ammonium cation and the by-product is referred to as a second alicyclic quaternary ammonium cation in some cases.

In view of the above, an ionic liquid in which a by-product is reduced as much as possible is preferably used as the solvent for the nonaqueous electrolyte of one embodiment of the present invention. Specifically, the amount of the by-product is preferably less than or equal to 1 wt % per unit weight of the solvent for the nonaqueous electrolyte. Therefore, the nonaqueous electrolyte of one embodiment of the present invention includes an ionic liquid including the first alicyclic quaternary ammonium cation, the second alicyclic quaternary ammonium cation which has the same alicyclic skeleton as the first alicyclic quaternary ammonium cation and in which one of substitutes bonded to a nitrogen atom in the alicyclic skeleton is a substitute including a halogen element, and a counter anion to the first alicyclic quaternary ammonium cation and the second alicyclic quaternary ammonium cation; and a salt including carrier ions of the power storage device. In the ionic liquid, the amount of a salt including the second alicyclic quaternary ammonium cation is preferably less than or equal to 1 wt % per unit weight of the ionic liquid, or is preferably less than or equal to 0.8 wt % per unit weight of the nonaqueous electrolyte. It is more preferable that in the ionic liquid, the amount of the salt including the second alicyclic quaternary ammonium cation be less than or equal to 0.6 wt % per unit weight of the ionic liquid, or be less than or equal to 0.5 wt % per unit weight of the nonaqueous electrolyte.

In the alicyclic quaternary ammonium cation included in the ionic liquid, the number of carbon atoms in the alicyclic skeleton is preferably less than or equal to 5 in view of the stability, viscosity, and ion conductivity of a compound and ease of synthesis. In other words, a quaternary ammonium cation in which the length of a ring is shorter than that of a six-membered ring is preferably used.

As an example of the substituent included in the alicyclic skeleton, an electron donating substituent such as an alkyl group having 1 to 20 carbon atoms can be given. The alkyl group may be either a straight-chain alkyl group or a branched-chain alkyl group. Note that the substituent is not limited thereto as long as it has an electron donating property. The substituent is not even limited to an electron donating substituent. For example, the substituent may be a methoxy group, a methoxymethyl group, or a methoxyethyl group.

There is no particular limitation on the anion included in the ionic liquid, as long as the anion is a monovalent anion which forms the ionic liquid with the alicyclic quaternary ammonium cation. Examples of the anion include a monovalent imide anion, a monovalent methide anion, a perfluoroalkyl sulfonic acid anion, tetrafluoroborate ($BF_4^-$), and hexafluorophosphate ($PF_6^-$). As a monovalent imide anion, $(C_nF_{2n+1}SO_2)_2N^-$ (n=0 to 3), $CF_2(CF_2SO_2)_2N^-$, and the like can be given. As a perfluoroalkyl sulfonic acid anion, $(C_mF_{2m+1}SO_3)^-$ (m=0 to 4) and the like can be given.

In view of the above, an ionic liquid of one embodiment of the present invention is an ionic liquid including a quaternary ammonium cation represented by General Formula (G3) (main product), a quaternary ammonium cation represented by General Formula (G4) (by-product), and an anion selected from any of the above-described anions.

[Chemical Formula 3]

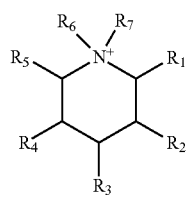
(G3)

In General Formula (G3), $R_1$ to $R_5$ each represent a hydrogen atom or an alkyl group having 1 to 20 carbon atoms, and $R_6$ and $R_7$ each represent an alkyl group having 1 to 4 carbon atoms.

[Chemical Formula 4]

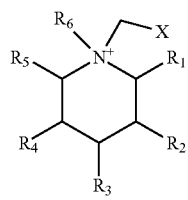
(G4)

In General Formula (G4), $R_1$ to $R_5$ each represent a hydrogen atom or an alkyl group having 1 to 20 carbon atoms, and $R_6$ represents an alkyl group having 1 to 4 carbon atoms. X represents any of the halogens.

Further, an ionic liquid of one embodiment of the present invention is an ionic liquid including a quaternary ammonium cation represented by General Formula (G5) (main product), a quaternary ammonium cation represented by General Formula (G6) (by-product), and an anion selected from any of the above-described anions.

[Chemical Formula 5]

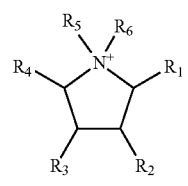
(G5)

In General Formula (G5), $R_1$ to $R_4$ each represent a hydrogen atom or an alkyl group having 1 to 20 carbon atoms, and $R_5$ and $R_6$ each represent an alkyl group having 1 to 4 carbon atoms.

[Chemical Formula 6]

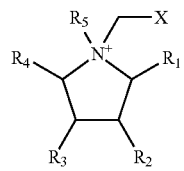
(G6)

In General Formula (G6), $R_1$ to $R_4$ each represent a hydrogen atom or an alkyl group having 1 to 20 carbon atoms, and $R_5$ represents an alkyl group having 1 to 4 carbon atoms. X represents any of the halogens.

Further, in the ionic liquid of one embodiment of the present invention, the amount of the quaternary ammonium cation that is the by-product and represented by General Formula (G4) or (G6) is preferably as low as possible. For example, the amount is preferably reduced to such an extent that peaks attributed to the by-product are not detected by measurement using a proton ($^1$H) NMR (the lower limit of detection). Although the details are described later, the amount can be decreased by using, as a reaction solvent, an organic solvent which does not include a halogen element in the synthesis of the ionic liquid of one embodiment of the present invention.

Note that as a nonaqueous solvent for the nonaqueous electrolyte of one embodiment of the present invention, one or both of an ionic liquid in which a quaternary ammonium cation has 5 carbon atoms and an ionic liquid in which a quaternary ammonium cation has 4 carbon atoms may be used. The nonaqueous solvent may include a plurality of ionic liquids which are represented by General Formula (G3) and have substituents in different positions of an alicyclic skeleton, or a plurality of ionic liquids which are represented by General Formula (G5) and have substituents in different positions of an alicyclic skeleton. The freezing point of the nonaqueous solvent is depressed more in the case where the nonaqueous solvent includes a plurality of ionic liquids as described above than in the case where the nonaqueous solvent includes only one ionic liquid. Thus, the use of a nonaqueous solvent including a plurality of ionic liquids enables a power storage device to be operated in a low-temperature environment, so that a power storage device which can be operated in a wide temperature range can be manufactured. Note that in the case where the nonaqueous solvent includes the plurality of ionic liquids, the amount of a salt including the quaternary ammonium cation that is a by-product is preferably less than or equal to 1 wt % per unit weight of the ionic liquid, or is preferably less than or equal to 0.8 wt % per unit weight of the nonaqueous electrolyte. It is more preferable that the amount of the salt including the quaternary ammonium cation that is the by-product be less than or equal to 0.6 wt % per unit weight of the ionic liquid, or be less than or equal to 0.5 wt % per unit weight of the nonaqueous electrolyte. Note that other than the ionic liquid, an organic solvent such as a cyclic ester may be mixed into the nonaqueous solvent.

The ionic liquid including the alicyclic quaternary ammonium cation represented by General Formula (G3) can be, for example, an ionic liquid including an alicyclic quaternary ammonium cation represented by General Formula (G1) in which $R_6$ and $R_7$ of the alicyclic quaternary ammonium cation in the ionic liquid including the alicyclic quaternary ammonium cation represented by General Formula (G3) are a methyl group and a propyl group, respectively. Note that the anion in the ionic liquid is an anion selected from the above-described anions.

[Chemical Formula 7]

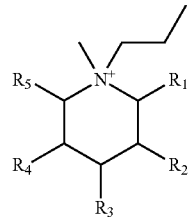

(G1)

In General Formula (G1), $R_1$ to $R_5$ each represent a hydrogen atom or an alkyl group having 1 to 20 carbon atoms.

Note that a quaternary ammonium cation included as the by-product when the alicyclic quaternary ammonium cation represented by General Formula (G1) is synthesized is an alicyclic quaternary ammonium cation represented by General Formula (G2).

[Chemical Formula 8]

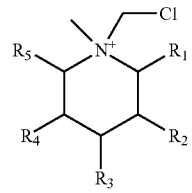

(G2)

In General Formula (G2), $R_1$ to $R_5$ each represent a hydrogen atom or an alkyl group having 1 to 20 carbon atoms.

Therefore, an example of the nonaqueous electrolyte of one embodiment of the present invention includes an ionic liquid including the alicyclic quaternary ammonium cation represented by General Formula (G1), the alicyclic quaternary ammonium cation represented by General Formula (G2), and a counter anion to the alicyclic quaternary ammonium cations represented by General Formulae (G1) and (G2) and a salt including carrier ions of a power storage device to be manufactured. In the ionic liquid, the amount of a salt including the alicyclic quaternary ammonium cation represented by General Formula (G2) is less than or equal to 1 wt % per unit weight of the ionic liquid, or is less than or equal to 0.8 wt % per unit weight of the nonaqueous electrolyte. It is more preferable that in the ionic liquid, the amount of the salt including the alicyclic quaternary ammonium cation represented by General Formula (G2) be less than or equal to 0.6 wt % per unit weight of the ionic liquid, or be less than or equal to 0.5 wt % per unit weight of the nonaqueous electrolyte.

Further, the ionic liquid including the alicyclic quaternary ammonium cation represented by General Formula (G5) can be, for example, an ionic liquid including an alicyclic quaternary ammonium cation represented by General Formula (G7) in which $R_5$ and $R_6$ of the alicyclic quaternary ammonium cation in the ionic liquid including the alicyclic quaternary ammonium cation represented by General Formula (G5) are a methyl group and a propyl group, respectively.

[Chemical Formula 9]

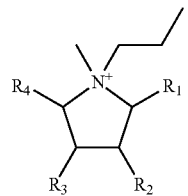

(G7)

In General Formula (G7), $R_1$ to $R_4$ each represent a hydrogen atom or an alkyl group having 1 to 20 carbon atoms.

Note that a quaternary ammonium cation included as the by-product when the alicyclic quaternary ammonium cation represented by General Formula (G7) is synthesized is an alicyclic quaternary ammonium cation represented by General Formula (G8).

[Chemical Formula 10]

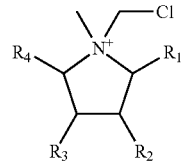

(G8)

In General Formula (G8), $R_1$ to $R_4$ each represent a hydrogen atom or an alkyl group having 1 to 20 carbon atoms.

Therefore, another example of the nonaqueous electrolyte of one embodiment of the present invention includes an ionic liquid including the alicyclic quaternary ammonium cation represented by General Formula (G7), the alicyclic quaternary ammonium cation represented by General Formula (G8), and a counter anion to the alicyclic quaternary ammonium cations represented by General Formulae (G7) and (G8) and a salt including carrier ions of a power storage device to be manufactured. In the ionic liquid, the amount of a salt including the alicyclic quaternary ammonium cation represented by General Formula (G8) is less than or equal to 1 wt % per unit weight of the ionic liquid, or is less than or equal to 0.8 wt % per unit weight of the nonaqueous electrolyte. It is more preferable that in the ionic liquid, the amount of the salt including the alicyclic quaternary ammonium cation represented by General Formula (G8) be less than or equal to 0.6 wt % per unit weight of the ionic liquid, or be less than or equal to 0.5 wt % per unit weight of the nonaqueous electrolyte.

In the ionic liquid including the alicyclic quaternary ammonium cation represented by General Formula (G1) or (G7), the amount of the quaternary ammonium cation that is the by-product and represented by General Formula (G2) or (G8) is preferably as low as possible. For example, the amount is preferably reduced to such an extent that peaks attributed to the by-product are not detected by measurement using a proton ($^1$H) NMR (the lower limit of detection). Although the details are described later, the amount can be decreased by using, as a reaction solvent, an organic solvent which does not include a halogen element in the synthesis of the ionic liquid of one embodiment of the present invention.

Note that $R_1$ to $R_5$ in the alicyclic quaternary ammonium cation represented by General Formula (G1) or (G3), or $R_1$ to $R_4$ in the alicyclic quaternary ammonium cation represented by General Formula (G5) or (G7) are electron donating substituents such as an alkyl group having 1 to 20 carbon atoms. The alkyl group may be either a straight-chain alkyl group or a branched-chain alkyl group. Note that $R_1$ to $R_5$ are not limited thereto as long as $R_1$ to $R_5$ have electron donating properties. Further, $R_1$ to $R_5$ are not even limited to electron donating substituents and may be, for example, a methoxy group, a methoxymethyl group, or a methoxyethyl group.

Here, reduction resistance and oxidation resistance of a nonaqueous solvent including an ionic liquid (specifically, a nonaqueous electrolyte including the nonaqueous solvent), which is included in a power storage device, is described. The nonaqueous solvent included in the power storage device preferably has excellent reduction resistance and oxidation resistance. In the case of low reduction resistance, the ionic liquid included in the nonaqueous solvent accepts electrons from a negative electrode to be reduced and decomposed. As a result, characteristics of the power storage device deteriorate. "Reduction of an ionic liquid" means that the ionic liquid accepts electrons from a negative electrode. Thus, by making it difficult particularly for a cation having a positive charge, which is included in the ionic liquid, to accept electrons, the reduction potential of the ionic liquid can be reduced. For this reason, the alicyclic quaternary ammonium cation represented by any of General Formulae (G1), (G3), (G5), and (G7) preferably has an electron donating substituent. Note that the reduction in reduction potential means an improvement in reduction resistance (also referred to as reduction stability).

In other words, when the above electron donating substituent is used as $R_1$ to $R_5$ in the alicyclic quaternary ammonium cation represented by General Formula (G1) or (G3), or $R_1$ to $R_4$ in the alicyclic quaternary ammonium cation represented by General Formula (G5) or (G7), inductive effects occur and electric polarization of the alicyclic quaternary ammonium cation is alleviated because of the inductive effects. Thus, it becomes difficult for the alicyclic quaternary ammonium cation to accept electrons, so that the reduction potential of the ionic liquid can be reduced.

Further, the reduction potential of the ionic liquid included in the nonaqueous electrolyte of one embodiment of the present invention is preferably lower than oxidation-reduction potential of lithium (Li/Li$^+$), which is a typical low potential negative electrode material.

However, as the number of electron donating substituents increases, the viscosity of the ionic liquid tends to increase. For this reason, the number of electron donating substituents is preferably adjusted depending on the desired reduction potential and desired viscosity as appropriate.

When $R_1$ to $R_5$ in the alicyclic quaternary ammonium cation represented by General Formulae (G1) and (G3), or $R_1$ to $R_4$ in the alicyclic quaternary ammonium cation represented by General Formulae (G5) and (G7) are alkyl groups having 1 to 20 carbon atoms, the number of carbon atoms is preferably small (e.g., 1 to 4), in which case the viscosity of the ionic liquid can be reduced. As a result, the viscosity of the nonaqueous solvent of one embodiment of the present invention can be reduced.

Further, an organic solvent such as a cyclic ester, an acyclic ester, a cyclic ether, or an acyclic ether may be mixed into the ionic liquid including the alicyclic quaternary ammonium cations represented by General Formulae (G1) and (G3) or General Formulae (G5) and (G7) in order to decrease the viscosity. As the organic solvent, ethylene carbonate, diethyl carbonate, propylene carbonate, or the like can be given, for example. Moreover, the organic solvent may be a fluorinated cyclic ester, a fluorinated acyclic ester, a fluorinated cyclic ether, or a fluorinated acyclic ether. Note that in this specification, the fluorinated cyclic ester refers to a cyclic ester in which fluorine is substituted for hydrogen, as in a cyclic ester including alkyl fluoride. Therefore, in the fluorinated acyclic ester, the fluorinated cyclic ether, or the fluorinated acyclic ether, fluorine is substituted for hydrogen. With the use of a mixed solvent of the ionic liquid and the organic solvent as the solvent for the nonaqueous electrolyte, the ion conductivity of the nonaqueous electrolyte can be increased, and thus the power storage device can have favorable charging and discharging rate characteristics.

Oxidation potential of the ionic liquid changes depending on anionic species. Thus, in order to obtain an ionic liquid having high oxidation potential, the anion in the ionic liquid included in the nonaqueous electrolyte of one embodiment of the present invention is preferably a monovalent anion selected from $(C_nF_{2n+1}SO_2)_2N^-$ (n=0 to 3), $CF_2(CF_2SO_2)_2N^-$, and $(C_mF_{2m+1}SO_3)^-$ (m=0 to 4). Note that the high oxidation potential means an improvement in oxidation resistance (also referred to as oxidation stability). The oxidation resistance is improved by the interaction between a cation in which electric polarization is alleviated because of an electron donating substituent and the anion described above.

Thus, by using the ionic liquid having improved reduction resistance and oxidation resistance (widened oxidation-reduction potential window) in the nonaqueous electrolyte of one embodiment of the present invention, decomposition of the ionic liquid due to charging and discharging can be suppressed. Thus, the use of the nonaqueous electrolyte of one embodiment of the present invention enables a highly reliable power storage device which has favorable cycle characteristics to be manufactured. Moreover, the use of the nonaqueous electrolyte of one embodiment of the present invention allows selection of a low potential negative electrode material and a high potential positive electrode material, so that a power storage device which has high energy density can be manufactured.

Further, in the nonaqueous electrolyte of one embodiment of the present invention, by reducing the by-product represented by General Formula (G2), (G4), (G6), or (G8), decomposition of the by-product due to charging and discharging can be suppressed. Thus, with the use of the nonaqueous electrolyte of one embodiment of the present invention, a power storage device in which deterioration in the characteristics due to the decomposition of the by-product is suppressed can be manufactured. Specifically, a power storage device having favorable cycle characteristics and high reliability even in an operating environment at relatively high temperature can be manufactured.

Meanwhile, the nonaqueous electrolyte of one embodiment of the present invention includes the ionic liquid which has non-flammability and non-volatility; thus, the nonaqueous electrolyte is difficult to ignite even when the internal temperature of a power storage device is increased. Thus, the use of the nonaqueous electrolyte of one embodiment of the present invention enables a power storage device with a high level of safety to be manufactured.

<Synthesis Method of Ionic Liquid>

Here, a method for synthesizing the ionic liquid described in this embodiment is described. A variety of reactions can be applied to the method for synthesizing the ionic liquid described in this embodiment. For example, the ionic liquid including the alicyclic quaternary ammonium cation represented by General Formula (G1) can be synthesized by a synthesis method described below. Here, an example is described referring to Synthesis Scheme (S-1). Note that the method for synthesizing the ionic liquid described in this embodiment is not limited to the synthesis method below.

[Chemical Formula 11]

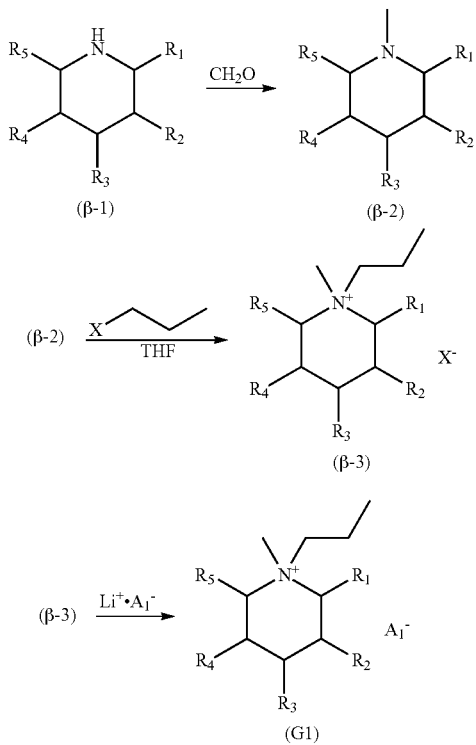

In Synthesis Scheme (S-1), the reaction from General Formula (β-1) to General Formula (β-2) is alkylation of amine by an amine compound and a carbonyl compound in the presence of hydride. For example, excessive formic acid can be used as the hydride source. Here, $CH_2O$ is used as the carbonyl compound.

In Synthesis Scheme (S-1), the reaction from General Formula (β-2) to General Formula (β-3) is alkylation by a tertiary amine compound and an alkyl halide compound, which synthesizes a quaternary ammonium salt. Here, propane halide is used as the alkyl halide compound. Note that X represents halogen, and the halogen is preferably bromine or iodine, more preferably iodine, in terms of high reactivity.

In the reaction from General Formula (β-2) to General Formula (β-3), when an organic solvent including a halogen element, such as dichloromethane (methylene chloride), is used as a reaction solvent, in addition to a quaternary ammonium salt represented by General Formula (β-3) that is a main product, a quaternary ammonium salt including the quaternary ammonium cation represented by General Formula (G2) is synthesized as a by-product.

In view of the above, in the reaction from General Formula (β-2) to General Formula (β-3), an organic solvent which does not include a halogen element in the structural formula, such as tetrahydrofuran (THF) or toluene, is used as the reaction solvent; thus, the amount of the quaternary ammonium cation represented by General Formula (G2) in the ionic liquid can be reduced. Moreover, the by-product content can be reduced to such an extent that peaks attributed to the quaternary ammonium cation are not detected by measurement using a proton ($^1$H) NMR (the lower limit of detection).

Through ion exchange between the quaternary ammonium salt represented by General Formula (β-3) and a desired metal salt including $A_1^-$, the ionic liquid including the alicyclic quaternary ammonium cation represented by General Formula (G1) can be obtained. Examples of $A_1^-$ include a monovalent imide anion, a monovalent methide anion, a perfluoroalkyl sulfonic acid anion, tetrafluoroborate ($BF_4^-$), and hexafluorophosphate ($PF_6^-$). As the monovalent imide anion, $(C_nF_{2n+1}SO_2)_2N^-$ (n=0 to 3), $CF_2(CF_2SO_2)_2N^-$, or the like is given. As the perfluoroalkyl sulfonic acid anion, $(C_mF_{2m+1}SO_3)^-$ (m=0 to 4) or the like is given.

A variety of reactions can be applied to the ionic liquid including the alicyclic quaternary ammonium cation represented by General Formula (G4). Here, an example is described referring to Synthesis Scheme (S-2). Note that the method for synthesizing the ionic liquid described in this embodiment is not limited to the synthesis method below.

[Chemical Formula 12]

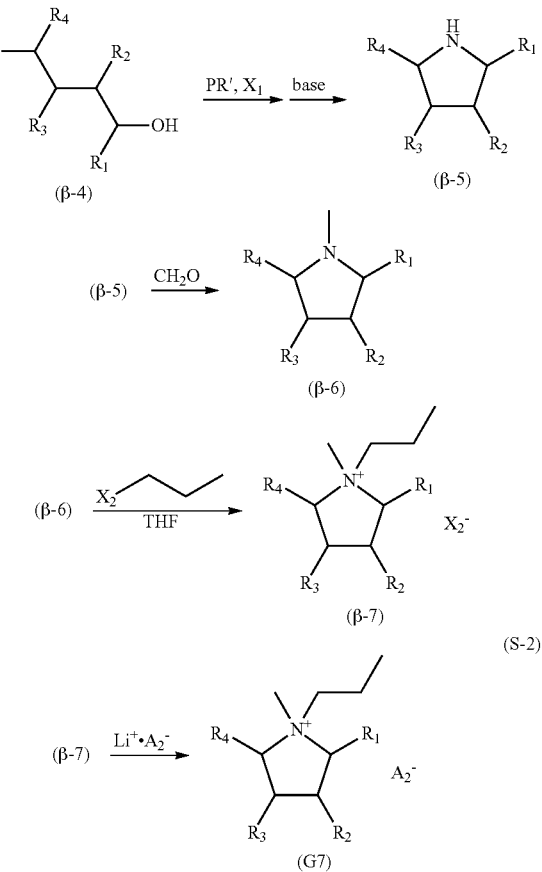

In Synthesis Scheme (S-2), a reaction from General Formula (β-4) to General Formula (β-5) is a ring closure reaction of amino alcohol which passes through halogenation using a halogen source and trisubstituted phosphine such as trialkylphosphine. Note that PR' represents trisubstituted phosphine and $X_1$ represents a halogen source. As the halogen source, carbon tetrachloride, carbon tetrabromide, iodine, iodomethane, or the like can be used. Here, triphenylphosphine is used as the trisubstituted phosphine and carbon tetrachloride is used as the halogen source.

In Synthesis Scheme (S-2), the reaction from General Formula (β-5) to General Formula (β-6) is alkylation of amine by an amine compound and a carbonyl compound in the presence of hydride. For example, excessive formic acid can be used as the hydride source. Here, $CH_2O$ is used as the carbonyl compound.

In Synthesis Scheme (S-2), the reaction from General Formula (β-6) to General Formula (β-7) is alkylation by a tertiary amine compound and an alkyl halide compound, which synthesizes a quaternary ammonium salt. Here, propane halide is used as the alkyl halide compound. Further, $X_2$ represents a halogen. The halogen is preferably bromine or iodine, more preferably iodine, in terms of high reactivity.

In the reaction from General Formula (β-6) to General Formula (β-7), when an organic solvent including a halogen element, such as dichloromethane (methylene chloride), is used as a reaction solvent, in addition to a quaternary ammonium salt represented by General Formula (β-7) that is a main product, a quaternary ammonium salt including the quaternary ammonium cation represented by General Formula (G8) is synthesized as a by-product.

In view of the above, in the reaction from General Formula (β-6) to General Formula (β-7), an organic solvent which does not include a halogen element in the structural formula, such as tetrahydrofuran (THF) or toluene, is used as the reaction solvent; thus, the amount of the quaternary ammonium cation represented by General Formula (G8) in the ionic liquid can be reduced. Moreover, the by-product content can be reduced to such an extent that peaks attributed to the quaternary ammonium cation are not detected by measurement using a proton ($^1H$) NMR (the lower limit of detection).

Through ion exchange between the quaternary ammonium salt represented by General Formula (β-7) and a desired metal salt including $A_2^-$, the ionic liquid including the quaternary ammonium cation represented by General Formula (G7) can be obtained. An example of the metal salt that can be used includes a potassium salt. Note that $A_2^-$ is similar to $A_1^{31}$ described in Synthesis Scheme (S-1).

As described above, an ionic liquid having a reduced amount of alicyclic quaternary ammonium cation in which a substituent including a halogen element is bonded to a nitrogen atom is used as the solvent for the nonaqueous electrolyte; thus, a power storage device in which deterioration in the characteristics due to decomposition of the alicyclic quaternary ammonium cation is suppressed can be manufactured. Specifically, a power storage device having favorable cycle characteristics and high reliability even in an operating environment at relatively high temperature can be manufactured.

This embodiment can be implemented in appropriate combination with any of the structures described in the other embodiments.

Embodiment 2

In this embodiment, a power storage device of one embodiment of the present invention and a method for manufacturing the power storage device are described. The power storage device of one embodiment of the present invention includes a positive electrode, a negative electrode, a nonaqueous electrolyte, and a separator. In this embodiment, a coin-type secondary battery is described as an example.

<Structure of Coin-type Secondary Battery>

FIG. 1A is a perspective view of a coin-type secondary battery 100. In the coin-type secondary battery 100, a housing 111 is provided over a housing 109 with a gasket 121 provided therebetween. The housings 109 and 111 have conductivity and thus serve as external terminals.

Figure 1B:
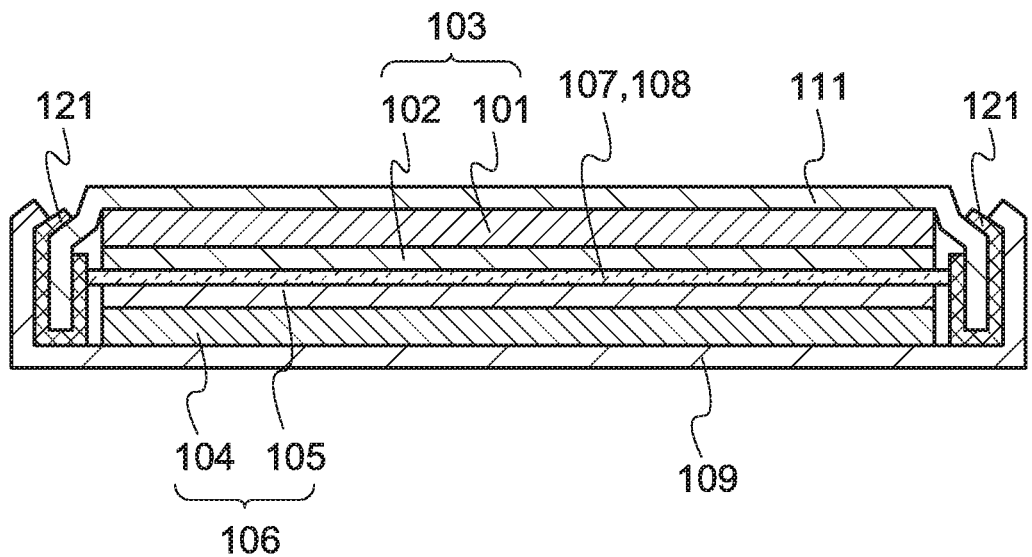

FIG. 1B is a cross-sectional view of the coin-type secondary battery 100 in the direction perpendicular to a top surface of the housing 111.

The coin-type secondary battery 100 includes a negative electrode 103 including a negative electrode current collector 101 and a negative electrode active material layer 102, a positive electrode 106 including a positive electrode current collector 104 and a positive electrode active material layer 105, and a separator 108 sandwiched between the negative electrode 103 and the positive electrode 106. Note that a nonaqueous electrolyte 107 is included in the separator 108. The positive electrode current collector 104 and the negative electrode current collector 101 are connected to the housing 109 and the housing 111, respectively. An end portion of the housing 111 is embedded in the gasket 121, whereby the isolation between the housing 109 and the housing 111 is maintained by the gasket 121.

The detailed description of the coin-type secondary battery 100 is given below.

The positive electrode current collector 104 can be formed using a material having high conductivity such as a metal typified by stainless steel, gold, platinum, zinc, iron, copper, aluminum, or titanium, or an alloy thereof. Alternatively, the positive electrode current collector 104 can be formed using an aluminum alloy to which an element which improves heat resistance, such as silicon, titanium, neodymium, scandium, or molybdenum, is added. Further alternatively, the positive electrode current collector 104 may be formed using a metal element which forms silicide by reacting with silicon. Examples of the metal element which forms silicide by reacting with silicon include zirconium, titanium, hafnium, vanadium, niobium, tantalum, chromium, molybdenum, tungsten, cobalt, nickel, and the like. The positive electrode current collector 104 can have a foil-like shape, a plate-like shape (sheet-like shape), a net-like shape, a punching-metal shape, an expanded-metal shape, or the like as appropriate.

As the positive electrode active material layer 105, a substance including carrier ions of the coin-type secondary battery 100 and a transition metal (i.e., positive electrode active material) is used, for example.

Alkali metal ions, alkaline earth metal ions, beryllium ions, or magnesium ions can be used as the carrier ions of the coin-type secondary battery 100. Examples of the alkali metal ions include lithium ions, sodium ions, and potassium ions. Examples of the alkaline earth metal ions include calcium ions, strontium ions, and barium ions.

As the positive electrode active material, a material represented by General Formula $A_hM_iPO_j$ (h>0, i>0, j>0) can also be used, for example. Here, A represents, for example, an alkali metal such as lithium, sodium, or potassium; an alkaline earth metal such as calcium, strontium, or barium; beryllium; or magnesium. M represents a transition metal such as iron, nickel, manganese, or cobalt, for example. Thus, examples of the material represented by General Formula $A_hM_iPO_j$ (h>0, i>0, j>0) include lithium iron phosphate and sodium iron phosphate. Note that one or more of any of the above-described metals can be selected as A or M.

Alternatively, a material represented by General Formula $A_hM_iO_j$ (h>0, i>0, j>0) can be used. Here, A represents, for example, an alkali metal such as lithium, sodium, or potassium; an alkaline earth metal such as calcium, strontium, or barium; beryllium; or magnesium. M represents a transition metal such as iron, nickel, manganese, or cobalt, for example. Thus, examples of the material represented by General Formula $A_hM_iO_j$ (h>0, i>0, j>0) include lithium cobaltate, lithium manganate, and lithium nickelate. Note that one or more of any of the above-described metals can be selected as A or M.

In the case where lithium ions are used as the carrier ions of the coin-type secondary battery 100 and thus the coin-type secondary battery 100 serves as a coin-type lithium secondary battery, a positive electrode active material including lithium is preferably selected for the positive electrode active material layer 105. In other words, A in General Formula $A_hM_iPO_j$ (h>0, i>0, j>0) or $A_hM_iO_j$ (h>0, i>0, j>0) is preferably lithium.

Further, a binding body including a conductive additive (e.g., acetylene black (AB)), a binder (e.g., polyvinylidene fluoride (PVDF)), and the like may be used as the positive electrode active material layer 105. In this specification, the term "positive electrode active material layer" refers to a layer at least including the positive electrode active material, and the positive electrode active material including a conductive additive, a binder, and the like is also referred to as the "positive electrode active material layer."

Note that the conductive additive is not limited to the above-described material, and as the conductive additive, an electron-conductive material can be used as long as it is not chemically changed in the power storage device. For example, a carbon-based material such as graphite or carbon fibers; a metal material such as copper, nickel, aluminum, or silver; or a powder or fiber of a mixture of the carbon-based material and the metal material can be used.

As the binder, polysaccharides such as starch, carboxymethyl cellulose, hydroxypropyl cellulose, regenerated cellulose, and diacetyl cellulose; vinyl polymers such as polyvinyl chloride, polyvinyl pyrrolidone, polytetrafluoroethylene, polyvinylidene fluoride, polyethylene, polypropylene, polyvinyl alcohol, ethylene-propylene-diene monomer (EPDM) rubber, sulfonated EPDM rubber, styrene-butadiene rubber, butadiene rubber, and fluorine rubber; polyether such as polyethylene oxide; and the like can be given.

In the positive electrode active material layer 105, graphene or multilayer graphene may be used instead of the conductive additive and the binder. Note that in this specification, the graphene refers to a one-atom-thick sheet of carbon molecules having $sp^2$ bonds. Further, the multilayer graphene refers to a stack of 2 to 100 sheets of graphene. The graphene and the multilayer graphene may contain less than or equal to 15 at. % of an element other than carbon, such as oxygen or hydrogen. Note that the graphene and the multilayer graphene may contain an alkali metal such as potassium.

Figure 2A:
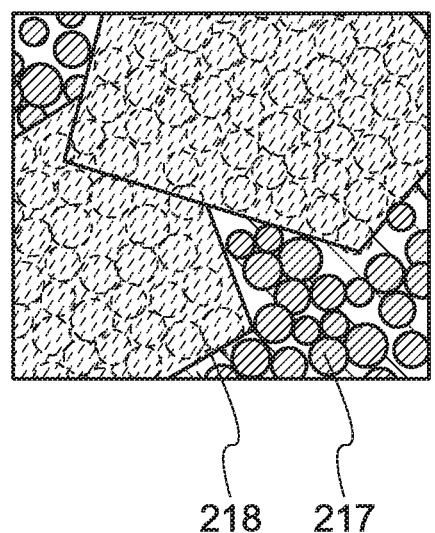
FIGS. 2A and 2B are a plan view and a cross-sectional view illustrating an electrode structure of a secondary battery of one embodiment of the present invention.

FIG. 2A is a plan view of the positive electrode active material layer 105 using the graphene instead of the conductive additive and the binder. The positive electrode active material layer 105 in FIG. 2A includes a positive electrode active material 217 which is a particle and graphenes 218 which cover a plurality of particles of the positive electrode active material 217 and at least partly surround the plurality of particles of the positive electrode active material 217. The different graphenes 218 cover surfaces of the plurality of particles of the positive electrode active material 217. Note that the positive electrode active material 217 may be exposed in part of the positive electrode active material layer 105.

Graphene is chemically stable and has favorable electric characteristics. Graphene has high conductivity because six-membered rings each composed of carbon atoms are connected in the planar direction. That is, graphene has high conductivity in the planar direction. Graphene has a sheet-like shape and a gap is provided between stacked graphene layers in the direction parallel to the plane, so that ions can transfer in the gap. However, the transfer of ions in the direction perpendicular to the graphene layers is difficult.

The size of the particle of the positive electrode active material 217 is preferably greater than or equal to 20 nm and less than or equal to 100 nm. Note that the size of the particle of the positive electrode active material 217 is preferably smaller because electrons transfer in the positive electrode active material 217.

Sufficient characteristics can be obtained even when the surface of the positive electrode active material 217 is not covered with a graphite layer; however, it is preferable to use both the graphene and the positive electrode active material covered with a graphite layer because carriers transfer hopping between the positive electrode active materials, so that current flows.

Figure 2B:
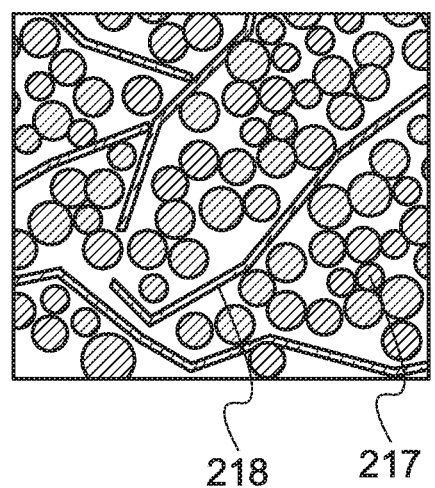

FIG. 2B is a cross-sectional view of part of the positive electrode active material layer 105 in FIG. 2A. The positive electrode active material layer 105 in FIG. 2A contains the positive electrode active material 217 and the graphenes 218 which cover the positive electrode active material 217. The graphenes 218 each have a linear shape when observed in the cross-sectional view. A plurality of particles of the positive electrode active material is at least partly surrounded with one graphene or plural graphenes. That is, the plurality of particles of the positive electrode active material exists within one graphene or among plural graphenes. Note that the graphene has a bag-like shape, and the plurality of particles of the positive electrode active material is surrounded with the bag-like portion in some cases. In addition, the plurality of particles of the positive electrode active material is not covered with the graphenes and partly exposed in some cases.

As the thickness of the positive electrode active material layer 105, a desired thickness is selected from the range of 20 μm to 100 μm. It is preferable to adjust the thickness of the positive electrode active material layer 105 as appropriate so that a crack and separation are not caused.

As an example of the positive electrode active material, a material whose volume is expanded by insertion of carrier ions is given. In a power storage device using such a material, a positive electrode active material layer gets vulnerable and is partly pulverized or collapsed by charging and discharging, resulting in lower reliability of the power storage device. However, in the positive electrode active material layer using the graphene or multilayer graphene, even when the volume of the positive electrode active material expands because of charging and discharging, the graphene is provided in the periphery of the particles of the positive electrode active material; thus, the positive electrode active material layer is prevented from being pulverized or collapsed. That is to say, the graphene or multilayer graphene has a function of maintaining the bond between the particles of the positive electrode active material even when the volume of the positive electrode active material fluctuates by charging and discharging. Therefore, the power storage device can have high reliability.

The use of the graphene or multilayer graphene instead of a conductive additive and a binder leads to a reduction in the amount of the conductive additive and the binder in the positive electrode 106. In other words, the weight of the positive electrode 106 can be reduced; consequently, the capacity of the battery per unit weight of the electrode can be increased.

Note that the positive electrode active material layer 105 may contain acetylene black particles having a volume 0.1 to 10 times as large as that of the graphene, carbon particles having a one-dimensional expansion (e.g., carbon nanofibers), or other known binders.

Next, the negative electrode current collector 101 can be formed using a metal material such as gold, platinum, zinc, iron, copper, aluminum, nickel, titanium, or an alloy material including a plurality of these metal materials (e.g., stainless steel). Note that the negative electrode current collector 101 is preferably formed using an aluminum alloy to which an element which improves heat resistance, such as silicon, titanium, neodymium, scandium, or molybdenum, is added. Alternatively, the negative electrode current collector 101 may be formed using a metal material which forms silicide by reacting with silicon. Examples of the metal material which forms silicide by reacting with silicon include zirconium, titanium, hafnium, vanadium, niobium, tantalum, chromium, molybdenum, tungsten, cobalt, and nickel. The negative electrode current collector 101 can have a foil-like shape, a plate-like shape (sheet-like shape), a net-like shape, a punching-metal shape, an expanded-metal shape, or the like as appropriate.

There is no particular limitation on a material used for the negative electrode active material layer 102 as long as the material can dissolve and precipitate lithium or into/from which lithium ions can be inserted and extracted (i.e., negative electrode active material). For example, lithium, aluminum, a carbon-based material, tin, silicon, a silicon alloy, or germanium can be used as the negative electrode active material. Alternatively, a compound containing one or more of the above-described materials may be used. For the carbon-based material into/from which lithium ions can be intercalated and deintercalated, a graphite powder or graphite fiber (the graphite includes natural graphite, artificial graphite, or the like), or amorphous carbon such as carbon black, active carbon, soft carbon, or hard carbon can be used. The amount of lithium ions occluded by silicon, a silicon alloy, germanium, lithium, aluminum, and tin is larger than that by the carbon-base material. Therefore, the negative electrode active material layer 102 can be formed using a less amount of material, which enables reductions in cost and the size of the coin-type secondary battery 100.

Alternatively, one of the above-described materials which are applicable to the negative electrode active material layer 102 may be used alone as the negative electrode 103 without the use of the negative electrode current collector 101.

Further alternatively, graphene or multilayer graphene may be formed on the surface of the negative electrode active material layer 102. In that case, it is possible to suppress influence of dissolution or precipitation of lithium or occlusion (insertion) or release (extraction) of lithium ions on the negative electrode active material layer 102. The influence refers to pulverization or separation of the negative electrode active material layer 102 which is caused by expansion or contraction of the negative electrode active material layer 102.

As the nonaqueous electrolyte 107, the nonaqueous electrolyte described in Embodiment 1 can be used. In this embodiment, a lithium salt including lithium ions that are carrier ions is used so that the coin-type secondary battery 100 serves as a lithium secondary battery. As the lithium salt, any of the lithium salts described in Embodiment 1 can be used.

Note that as the salt included in the nonaqueous electrolyte 107, a salt can be used as long as it includes any of the above-described carrier ions and corresponds to the positive electrode active material layer 105. For example, when carrier ions of the coin-type secondary battery 100 are alkali metal ions other than lithium ions or alkaline earth metal ions, an alkali metal salt (e.g., a sodium salt or a potassium salt), an alkaline earth metal salt (e.g., a calcium salt, a strontium salt, or a barium salt), a beryllium salt, a magnesium salt, or the like may be used. The nonaqueous electrolyte 107 including the salt has the freezing point lower than that of an ionic liquid (solvent). Thus, the coin-type secondary battery 100 including the nonaqueous electrolyte 107 can be operated in a low-temperature environment, that is, the operating temperature can be widened.

Alternatively, the nonaqueous electrolyte described in Embodiment 1 may be gelled to be used as the nonaqueous electrolyte 107. With the use of the gelled nonaqueous electrolyte, safety against liquid leakage and the like is improved, and the coin-type secondary battery 100 can be made thin and lightweight. Note that there is no limitation on a high-molecular material used for gelation of the nonaqueous electrolyte as long as it can be used for the gelation of the nonaqueous electrolyte described in Embodiment 1. Examples of the high-molecular material include a silicon gel, an acrylic gel, an acrylonitrile gel, polyethylene oxide, polypropylene oxide, and a fluorine-based polymer.

As the separator 108, an insulating porous material is used. For example, paper; nonwoven fabric; a glass fiber; ceramics; or a synthetic fiber containing nylon (polyamide), vinylon (polyvinyl alcohol based fiber), polyester, acrylic, polyolefin, or polyurethane may be used. Note that a material which does not dissolve in the nonaqueous electrolyte 107 needs to be selected.

Although the coin-type secondary battery 100 which is sealed is described as the power storage device in this embodiment, the form of the power storage device is not limited thereto. That is, the power storage device of one embodiment of the present invention can have a variety of forms such as a laminated type, a cylindrical type, or a square type. Further, although the positive electrode 106, the negative electrode 103, and the separator 108 are stacked in the coin-type secondary battery 100, the positive electrode, the negative electrode, and the separator may be rolled up depending on the form of the power storage device.

<Method for Manufacturing Coin-Type Secondary Battery>

Next, a method for manufacturing the coin-type secondary battery 100 is described. First, a method for forming the positive electrode 106 is described.

Materials for the positive electrode current collector 104 and the positive electrode active material layer 105 are selected from the above-described materials. Here, lithium iron phosphate ($LiFePO_4$) is used as the positive electrode active material of the positive electrode active material layer 105.

The positive electrode active material layer 105 is formed over the positive electrode current collector 104. The positive electrode active material layer 105 may be formed by a coating method or a sputtering method using any of the above-described materials as a target. In the case of forming the positive electrode active material layer 105 by the coating method, a paste in which the positive electrode active material is mixed with a conductive additive, a binder, or the like is formed as slurry and then, the slurry is applied onto the positive electrode current collector 104 and dried. In the case of forming the positive electrode active material layer 105 by the coating method, pressure forming may also be employed, if necessary. In the above manner, the positive electrode 106 in which the positive electrode active material layer 105 is formed over the positive electrode current collector 104 can be formed.

In the case where the graphene or multilayer graphene is used in the positive electrode active material layer 105, at least the positive electrode active material and graphene oxide are mixed to form slurry, and the slurry is applied onto the positive electrode current collector 104 and dried. The drying is performed by heating in a reducing atmosphere. Thus, the positive electrode active material is baked and reduction treatment for extracting oxygen included in the graphene oxide can be performed, so that graphene can be formed. Note that in this specification, graphene oxide refers to a compound formed by oxidation of the above graphene or multilayer graphene. Further, in the case where graphene or multilayer graphene is formed by reduction of graphene oxide, oxygen included in the graphene oxide is not entirely extracted and partly remains in the graphene.

Next, a method for forming the negative electrode 103 is described.

Materials for the negative electrode current collector 101 and the negative electrode active material layer 102 (negative electrode active material) may be selected from the above-described materials. A coating method, a chemical vapor deposition method, or a physical vapor deposition method may be used to form the negative electrode active material layer 102 over the negative electrode current collector 101. Note that in the case where a conductive additive and a binder are used for the negative electrode active material layer 102, a material selected from the above-described materials can be used as appropriate.

Figure 3A:
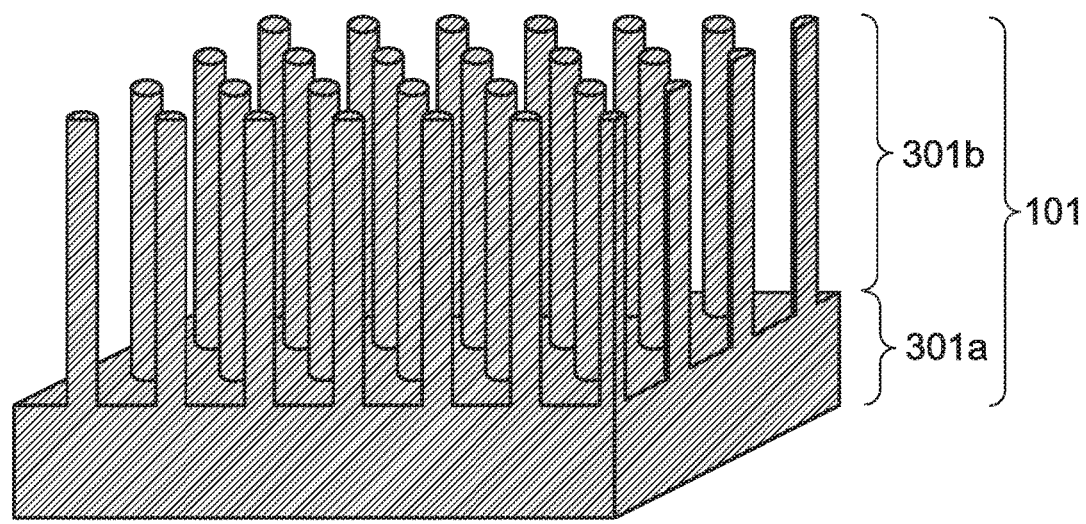
FIGS. 3A and 3B are perspective views illustrating a current collector structure and an electrode structure of a secondary battery of one embodiment of the present invention.

Here, other than the above-described shapes, the negative electrode current collector 101 may be processed to have a shape including protrusions and depressions as illustrated in FIG. 3A. FIG. 3A is a schematic cross-sectional view of an enlarged surface part of the negative electrode current collector. The negative electrode current collector 101 includes a plurality of protrusion portions 301b and a base portion 301a to which each of the plurality of protrusion portions is connected. Although the thin base portion 301a is illustrated in FIG. 3A, the base portion 301a is generally much thicker than the protrusion portions 301b.

The plurality of protrusion portions 301b extend in a direction substantially perpendicular to a surface of the base portion 301a. In this specification, although the angle between the surface of the base portion 301a and a center axis of the protrusion portion 301b in the longitudinal direction is preferably 90°, the term "substantially" means that a slight deviation from the perpendicular direction due to an error in leveling in a manufacturing process of the negative electrode current collector, step variation in a manufacturing process of the protrusion portions 301b, deformation due to repeated charging and discharging, and the like is acceptable. Specifically, the angle between the surface of the base portion 301a and the center axis of the protrusion portion 301b in the longitudinal direction is less than or equal to 90°±10°, preferably less than or equal to 90°±5°.

Note that the negative electrode current collector 101 including protrusions and depressions illustrated in FIG. 3A can be formed in such a manner that a mask is formed over the negative electrode current collector, the negative electrode current collector is etched with the use of the mask, and the mask is removed. Accordingly, in the case of forming the negative electrode current collector 101 including protrusions and depressions illustrated in FIG. 3A, titanium is preferably used for the negative electrode current collector 101. Titanium is a material very suitable for processing by dry etching and makes it possible to form protrusions and depressions with a high aspect ratio. Further, other than photolithography, the mask can be formed by an inkjet method, a printing method, or the like. In particular, the mask can be formed by nanoimprint lithography typified by thermal nanoimprint lithography and photo nanoimprint lithography.

Figure 3B:
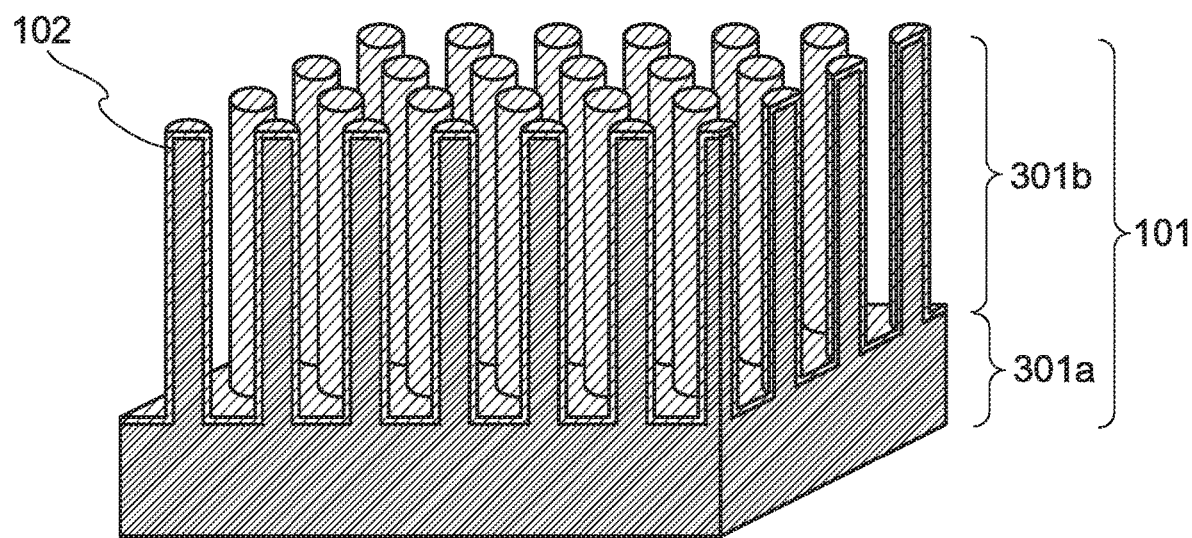

When the negative electrode active material layer 102 is formed over the negative electrode current collector 101 including protrusions and depressions illustrated in FIG. 3A, the negative electrode active material layer 102 is formed to cover the protrusions and depressions (see FIG. 3B).

Here, titanium foil is used for the negative electrode current collector 101, and silicon deposited by a chemical vapor deposition method or a physical vapor deposition method is used for the negative electrode active material layer 102.

In the case of using silicon as the negative electrode active material layer 102, amorphous silicon or crystalline silicon such as microcrystalline silicon, polycrystalline silicon, or single crystal silicon can be used as the silicon.

Alternatively, as the negative electrode active material layer 102, a layer obtained by forming microcrystalline silicon over the negative electrode current collector 101 and then removing amorphous silicon from the microcrystalline silicon by etching may be used. When the amorphous silicon is removed from the microcrystalline silicon, the surface area of the remaining microcrystalline silicon is increased. The microcrystalline silicon can be formed by, for example, a plasma chemical vapor deposition (CVD) method or a sputtering method.

Figure 4A:
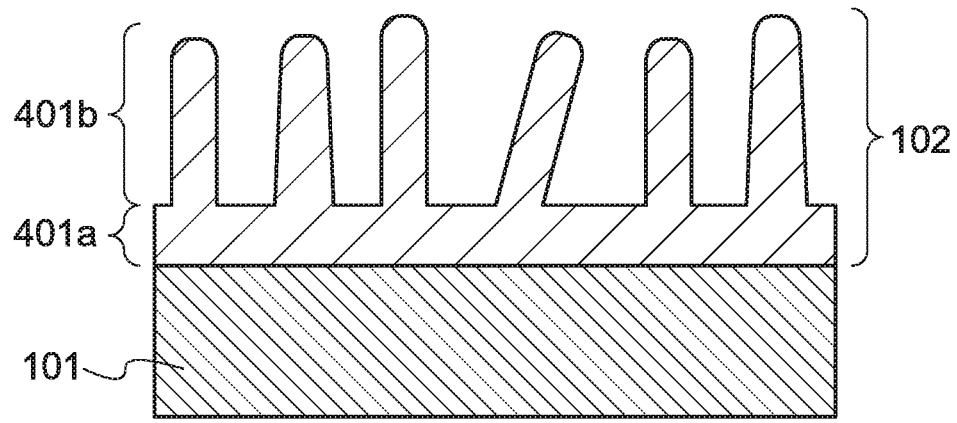
FIGS. 4A to 4C are cross-sectional views each illustrating an electrode structure of a secondary battery of one embodiment of the present invention.
Figure 4B:
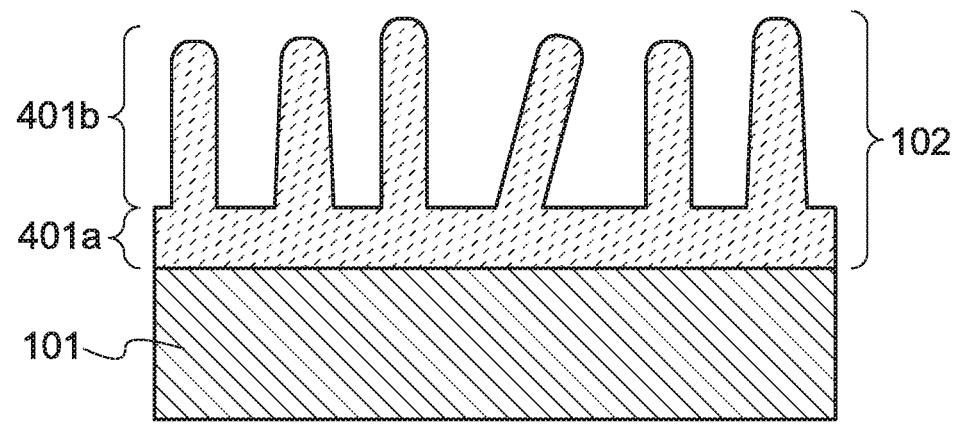
Figure 4C:
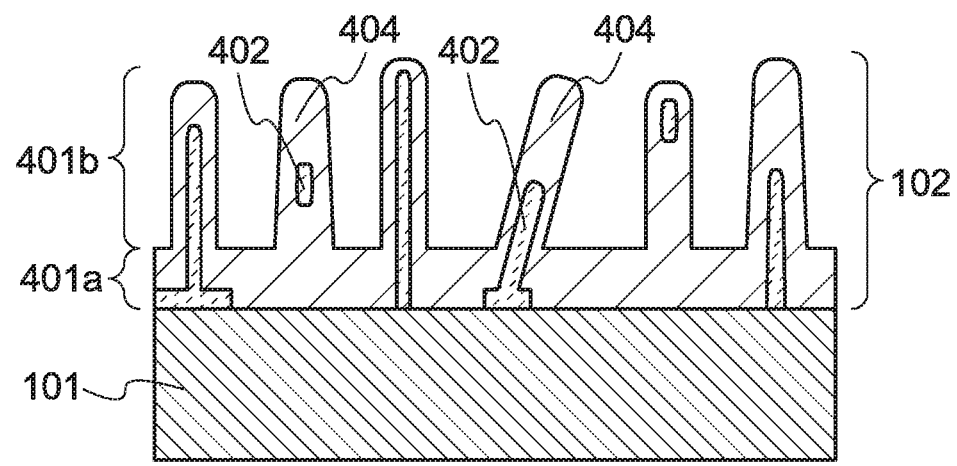

Further alternatively, the negative electrode active material layer 102 may be whisker-like silicon which is formed over the negative electrode current collector 101 by a low pressure (LP) CVD method (see FIGS. 4A to 4C). Note that in this specification, whisker-like silicon refers to silicon having a common portion 401a and a region 401b protruding from the common portion 401a like a whisker (or a string or a fiber).

When the whisker-like silicon is made of amorphous silicon, the volume of the whisker-like silicon is less likely to be changed due to occlusion and release of ions (e.g., stress due to volume expansion is relaxed), which can prevent pulverization or separation of the negative electrode active material layer due to repeated charging and discharging; thus, the cycle characteristics of the power storage device can be improved (see FIG. 4A).

When the whisker-like silicon is made of crystalline silicon such as microcrystalline silicon, polycrystalline silicon, or single crystal silicon, a crystal structure having excellent electron conductivity, excellent ion conductivity, and crystallinity is in contact with the current collector in a large area. Therefore, conductivity of the whole negative electrode can be improved, and the charging and discharging characteristics of the power storage device can be further improved (see FIG. 4B).

Further, the whisker-like silicon may include a core 402 made of crystalline silicon and an outer shell 404 made of amorphous silicon which covers the core (see FIG. 4C). In that case, the amorphous silicon that is the outer shell 404 has a characteristic in that the volume is less likely to be changed due to occlusion and release of ions (e.g., stress caused by expansion in volume is relieved). In addition, the crystalline silicon that is the core 402 has excellent electron conductivity and ion conductivity and has a characteristic in that the rate of occluding ions and the rate of releasing ions are high per unit mass. Therefore, with the use of the whisker-like silicon including the core 402 and the outer shell 404 as the negative electrode active material layer 102, the charging and discharging rate characteristics and cycle characteristics of the power storage device can be improved.

Note that in the common portion 401a, the crystalline silicon which forms the core 402 may be in contact with part of the top surface of the negative electrode current collector 101 as illustrated in FIG. 4C, or the entire top surface of the negative electrode current collector 101 may be in contact with the crystalline silicon.

The desired thickness of the negative electrode active material layer 102 is determined in the range of 20 μm to 100 μm.

Further, graphene or multilayer graphene can be formed on the surface of the negative electrode active material layer 102 in the following manner: the negative electrode current collector 101 which is provided with the negative electrode active material layer 102 is soaked together with a reference electrode in a solution containing graphene oxide, the solution is electrophoresed, and then heated so that reduction treatment is performed. Alternatively, the graphene or multilayer graphene can be formed on the surface of the negative electrode active material layer 102 by a dip coating method using the above solution; after dip coating is performed, reduction treatment is performed by heating.

Note that the negative electrode active material layer 102 may be predoped with lithium. Predoping with lithium can be performed in such a manner that a lithium layer is formed on the surface of the negative electrode active material layer 102 by a sputtering method. Alternatively, lithium foil is provided on the surface of the negative electrode active material layer 102, whereby the negative electrode active material layer 102 can be predoped with lithium.

The nonaqueous electrolyte 107 can be formed by the method described in Embodiment 1.

Then, the positive electrode 106, the separator 108, and the negative electrode 103 are immersed in the nonaqueous electrolyte 107. Next, the negative electrode 103, the separator 108, the gasket 121, the positive electrode 106, and the housing 111 are stacked in this order over the housing 109, and the housing 109 and the housing 111 are crimped to each other with a "coin cell crimper." Thus, the coin-type secondary battery 100 can be manufactured.

Note that a spacer and a washer may be provided between the housing 111 and the positive electrode 106 or between the housing 109 and the negative electrode 103 so that the connection between the housing 111 and the positive electrode 106 or between the housing 109 and the negative electrode 103 is enhanced.

Although the lithium secondary battery is described as an example of the power storage device in this embodiment, the power storage device of one embodiment of the present invention is not limited to this. For example, with the use of the nonaqueous electrolyte of one embodiment of the present invention, a lithium ion capacitor can be manufactured.

The lithium ion capacitor can be manufactured as follows: a material capable of reversibly adsorbing and extracting one or both of lithium ions and an anion is used to form a positive electrode; the above-described negative electrode active material, a conductive high molecule such as a polyacene organic semiconductor (PAS), or the like is used to form a negative electrode; and the nonaqueous electrolyte described in Embodiment 1 is used.

Further, an electric double layer capacitor can be manufactured as follows: the material capable of reversibly adsorbing and extracting one or both of lithium ions and an anion is used to form a positive electrode and a negative electrode; and the nonaqueous electrolyte described in Embodiment 1 is used.

This embodiment can be combined with the structure described in any of the other embodiments and examples as appropriate.

Embodiment 3

A power storage device of one embodiment of the present invention can be used as a power supply of a variety of electrical appliances operated by electric power.

Specific examples of electrical appliances including the power storage device of one embodiment of the present invention include display devices, lighting devices, desktop personal computers or laptop personal computers, image reproduction devices which reproduce a still image or a moving image stored in a recording medium such as a digital versatile disc (DVD), mobile phones, portable game machines, portable information terminals, e-book readers, video cameras, digital still cameras, high-frequency heating apparatus such as microwaves, electric rice cookers, electric washing machines, air-conditioning systems such as air conditioners, electric refrigerators, electric freezers, electric refrigerator-freezers, freezers for preserving DNA, and dialysis devices. In addition, moving objects driven by an electric motor using electric power from a power storage device are also included in the category of the electrical appliances. Examples of the moving objects include electric vehicles, hybrid vehicles which include both an internal-combustion engine and a motor, and motorized bicycles including motor-assisted bicycles.

In the electrical appliances, the power storage device of one embodiment of the present invention can be used as a power storage device for supplying enough electric power for almost the whole power consumption (such a power storage device is referred to as a main power supply). Alternatively, in the electrical appliances, the power storage device of one embodiment of the present invention can be used as a power storage device which can supply electric power to the electrical appliances when the supply of power from the main power supply or a commercial power supply is stopped (such a power storage device is referred to as an uninterruptible power supply). Further alternatively, in the electrical appliances, the power storage device of one embodiment of the present invention can be used as a power storage device for supplying electric power to the electrical appliances at the same time as the electric power supply from the main power supply or a commercial power supply (such a power storage device is referred to as an auxiliary power supply).

Figure 5:
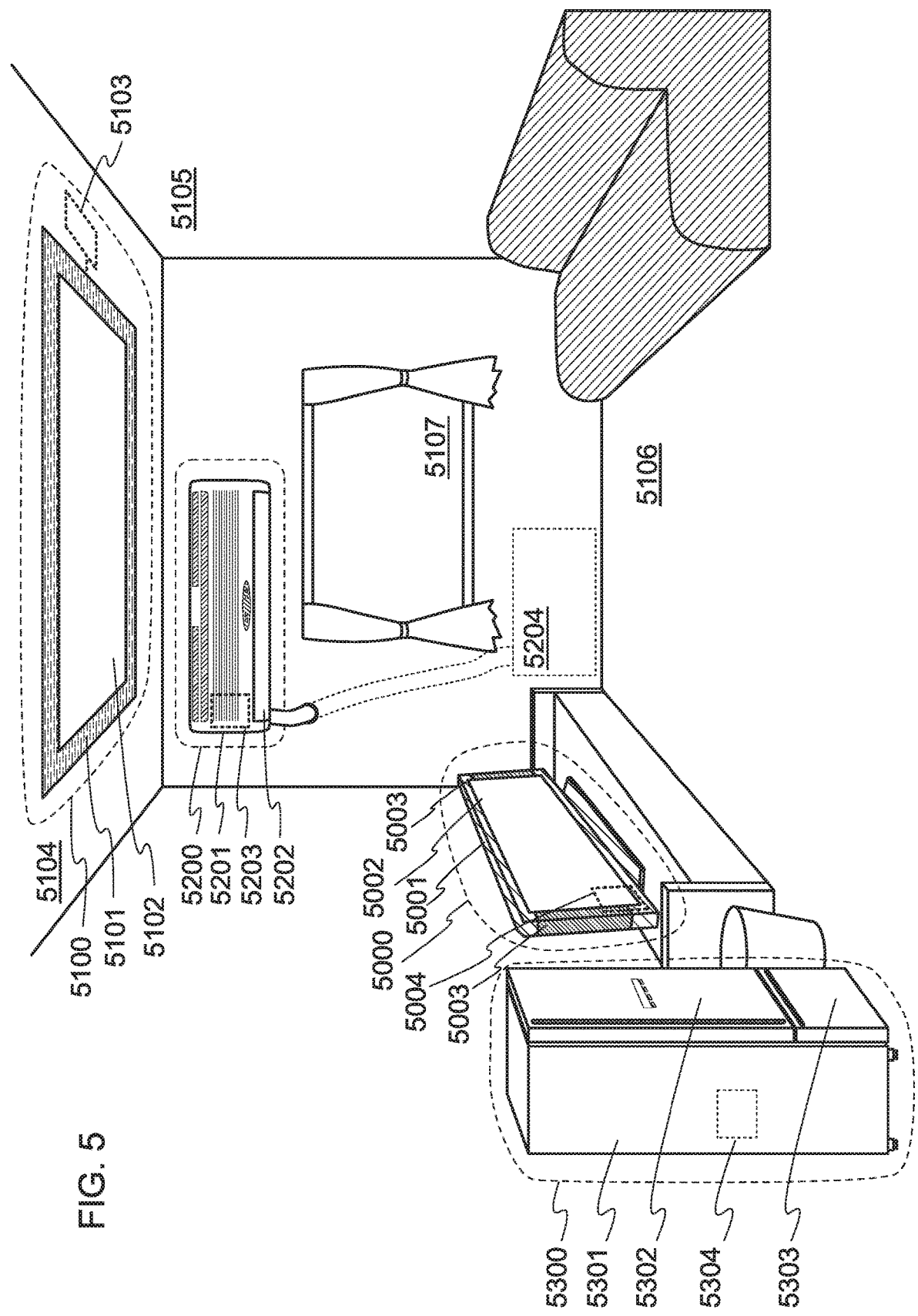
FIG. 5 is a diagram illustrating electrical appliances each including a power storage device of one embodiment of the present invention.

FIG. 5 illustrates specific structures of the electrical appliances. In FIG. 5, a display device 5000 is an example of an electrical appliance including a power storage device of one embodiment of the present invention. Specifically, the display device 5000 corresponds to a display device for TV broadcast reception and includes a housing 5001, a display portion 5002, speaker portions 5003, a power storage device 5004, and the like. The power storage device 5004 is provided in the housing 5001. The display device 5000 can receive electric power from a commercial power supply. Alternatively, the display device 5000 can use electric power stored in the power storage device 5004. Thus, the display device 5000 can be operated with the use of the power storage device 5004 as an uninterruptible power supply even when power cannot be supplied from a commercial power supply because of power failure or the like.

A semiconductor display device such as a liquid crystal display device, a light-emitting device in which a light-emitting element such as an organic EL element is provided in each pixel, an electrophoresis display device, a digital micromirror device (DMD), a plasma display panel (PDP), a field emission display (FED), and the like can be used for the display portion 5002.

Note that the display device includes, in its category, all of information display devices for personal computers, advertisement displays, and the like other than TV broadcast reception.

In FIG. 5, an installation lighting device 5100 is an example of an electrical appliance including a power storage device of one embodiment of the present invention. Specifically, the lighting device 5100 includes a housing 5101, a light source 5102, a power storage device 5103, and the like. FIG. 5 illustrates the case where the power storage device 5103 is provided in a ceiling 5104 on which the housing 5101 and the light source 5102 are installed; alternatively, the power storage device 5103 may be provided in the housing 5101. The lighting device 5100 can receive electric power from the commercial power supply. Alternatively, the lighting device 5100 can use electric power stored in the power storage device 5103. Thus, the lighting device 5100 can be operated with the use of the power storage device 5103 as an uninterruptible power supply even when power cannot be supplied from a commercial power supply because of power failure or the like.

Note that although the installation lighting device 5100 provided in the ceiling 5104 is illustrated in FIG. 5 as an example, the power storage device of one embodiment of the present invention can be used in an installation lighting device provided in, for example, a wall 5105, a floor 5106, a window 5107, or the like other than the ceiling 5104. Alternatively, the power storage device can be used in a tabletop lighting device and the like.

As the light source 5102, an artificial light source which provides light artificially by using electric power can be used. Specifically, a discharge lamp such as an incandescent lamp and a fluorescent lamp, and a light-emitting element such as an LED and an organic EL element are given as examples of the artificial light source.

In FIG. 5, an air conditioner including an indoor unit 5200 and an outdoor unit 5204 is an example of an electrical appliance including a power storage device of one embodiment of the present invention. Specifically, the indoor unit 5200 includes a housing 5201, a ventilation duct 5202, a power storage device 5203, and the like. FIG. 5 illustrates the case where the power storage device 5203 is provided in the indoor unit 5200; alternatively, the power storage device 5203 may be provided in the outdoor unit 5204. Alternatively, the power storage devices 5203 may be provided in both the indoor unit 5200 and the outdoor unit 5204. The air conditioner can receive electric power from the commercial power supply. Alternatively, the air conditioner can use electric power stored in the power storage device 5203. In particular, in the case where the power storage devices 5203 are provided in both the indoor unit 5200 and the outdoor unit 5204, the air conditioner can be operated with the use of the power storage device of one embodiment of the present invention as an uninterruptible power supply even when power cannot be supplied from a commercial power supply because of power failure or the like.

Note that although the separated air conditioner including the indoor unit and the outdoor unit is illustrated in FIG. 5 as an example, the power storage device of one embodiment of the present invention can be used in an air conditioner in which the functions of an indoor unit and an outdoor unit are integrated in one housing.

In FIG. 5, an electric refrigerator-freezer 5300 is an example of an electrical appliance including a power storage device of one embodiment of the present invention. Specifically, the electric refrigerator-freezer 5300 includes a housing 5301, a door for a refrigerator 5302, a door for a freezer 5303, and a power storage device 5304, and the like. The power storage device 5304 is provided in the housing 5301 in FIG. 5. The electric refrigerator-freezer 5300 can receive power from a commercial power supply. Alternatively, the electric refrigerator-freezer 5300 can use power stored in the power storage device 5304. Thus, the electric refrigerator-freezer 5300 can be operated with use of the power storage device of one embodiment of the present invention as an uninterruptible power supply even when electric power cannot be supplied from the commercial power supply because of power failure or the like.

Note that among the electrical appliances described above, a high-frequency heating apparatus such as a microwave and an electrical appliance such as an electric rice cooker require high electric power in a short time. The tripping of a circuit breaker of a commercial power supply in use of the electrical appliances can be prevented by using the power storage device of one embodiment of the present invention as an auxiliary power supply for supplying electric power which cannot be supplied enough by the commercial power supply.

In addition, in a time period when electrical appliances are not used, specifically when the proportion of the amount of power which is actually used to the total amount of power which can be supplied by a commercial power supply source (such a proportion referred to as usage rate of power) is low, power can be stored in the power storage device, whereby the usage rate of power can be reduced in a time period when the electrical appliances are used. In the case of the electric refrigerator-freezer 5300, electric power can be stored in the power storage device 5304 at night time when the temperature is low and the door for a refrigerator 5302 and the door for a freezer 5303 are not opened and closed. The power storage device 5304 is used as an auxiliary power supply in daytime when the temperature is high and the door for a refrigerator 5302 and the door for a freezer 5303 are opened and closed; thus, the usage rate of electric power in daytime can be reduced.

This embodiment can be implemented in appropriate combination with any of the structures described in the other embodiments.

Embodiment 4

Next, a portable information terminal which is an example of electrical appliances will be described with reference to FIGS. 6A to 6C.

Figure 6A:
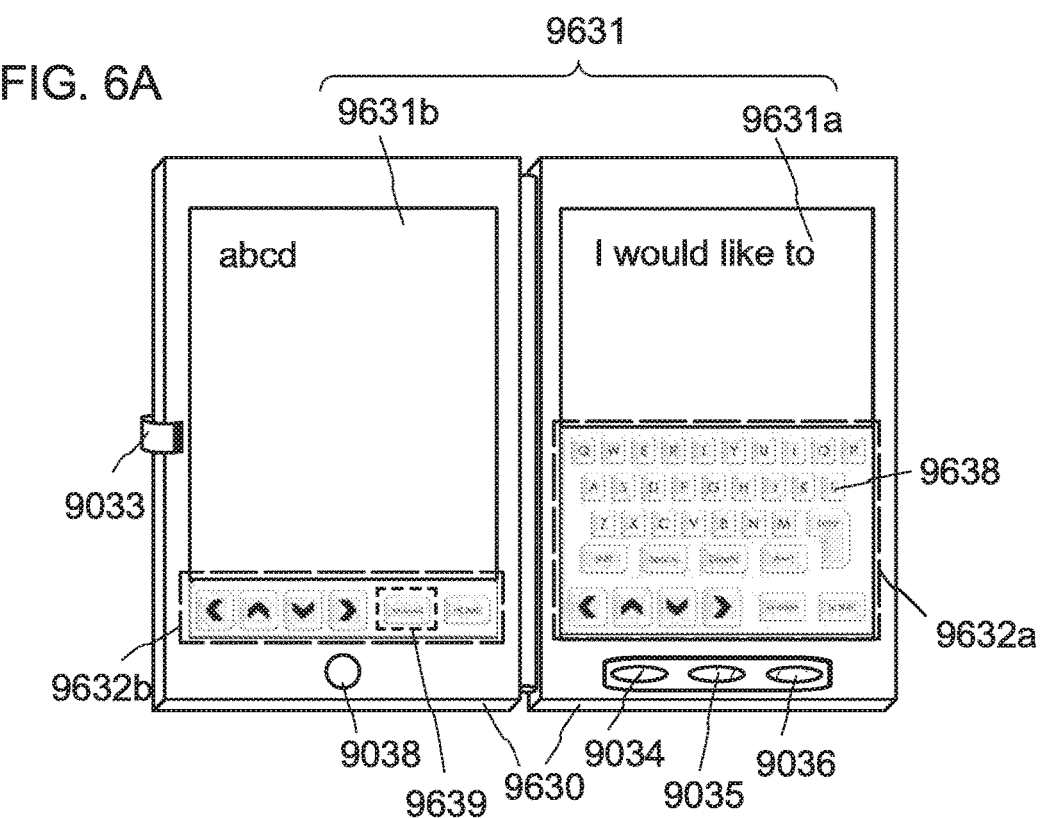
FIGS. 6A to 6C are diagrams illustrating an electrical appliance including a power storage device of one embodiment of the present invention.
Figure 6B:
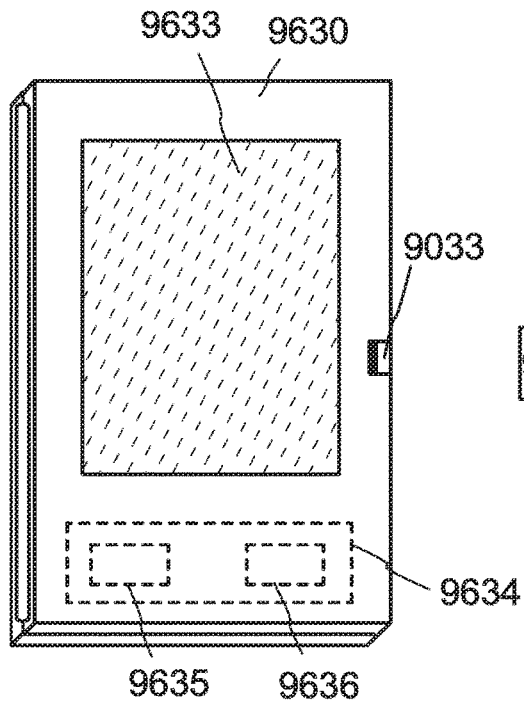

FIGS. 6A and 6B illustrate a tablet terminal that can be folded. In FIG. 6A, the tablet terminal is open (unfolded) and includes a housing 9630, a display portion 9631 including a display portion 9631a and a display portion 9631b, a switch 9034 for switching display modes, a power switch 9035, a switch 9036 for switching to power-saving mode, a fastener 9033, and an operation switch 9038.

Part of the display portion 9631a can be a touch panel region 9632a and data can be input when a displayed operation key 9638 is touched. Note that FIG. 6A illustrates, as an example, that half of the area of the display portion

9631a has only a display function and the other half of the area has a touch panel function. However, the structure of the display portion 9631a is not limited to this, and all the area of the display portion 9631a may have a touch panel function. For example, all the area of the display portion 9631a can display keyboard buttons and serve as a touch panel while the display portion 9631b can be used as a display screen.

As in the display portion 9631a, part of the display portion 9631b can be a touch panel region 9632b. Of operation keys displayed on the touch panel region 9632b, a switching button 9639 for showing/hiding a keyboard is touched with a finger, a stylus, or the like, so that keyboard buttons can be displayed on the display portion 9631b.

Touch input can be performed in the touch panel region 9632a and the touch panel region 9632b at the same time.

The switch 9034 for switching display modes can switch the display between portrait mode, landscape mode, and the like, and between monochrome display and color display, for example. With the switch 9036 for switching to power-saving mode, the luminance of display can be optimized in accordance with the amount of external light at the time when the tablet is in use, which is detected with an optical sensor incorporated in the tablet. The tablet may include another detection device such as a sensor for detecting orientation (e.g., a gyroscope or an acceleration sensor) in addition to the optical sensor.

Although FIG. 6A illustrates the example where the display area of the display portion 9631a is the same as that of the display portion 9631b, there is no particular limitation on the display portions 9631a and 9631b. They may differ in size and/or image quality. For example, one display panel may be capable of higher-definition display than the other display panel.

In FIG. 6B, the tablet terminal is close (folded) and includes the housing 9630, a solar cell 9633, a charge/discharge control circuit 9634, a battery 9635, and a DC-to-DC converter 9636. In FIG. 6B, a structure including the battery 9635 and the DC-to-DC converter 9636 is illustrated as an example of the charge/discharge control circuit 9634. The battery 9635 includes the power storage device of one embodiment of the present invention.

Since the tablet terminal is foldable, the housing 9630 can be closed when the tablet terminal is not used. As a result, the display portion 9631a and the display portion 9631b can be protected; thus, a tablet terminal which has excellent durability and excellent reliability also in terms of long-term use can be provided.

The tablet terminal illustrated in FIGS. 6A and 6B can also have a function of displaying various kinds of data (e.g., a still image, a moving image, and a text image), a function of displaying a calendar, a date, the time, or the like on the display portion, a touch-input function of operating or editing data displayed on the display portion by touch input, a function of controlling processing by various kinds of software (programs), and the like.

The solar cell 9633, which is attached on the surface of the tablet terminal, supplies electric power to the touch panel, the display portion, an image signal processor, or the like. Note that the solar cell 9633 can be provided on one or both surfaces of the housing 9630, so that the battery 9635 can be charged efficiently. The use of the power storage device of one embodiment of the present invention as the battery 9635 has advantages such as a reduction in size.

The structure and operation of the charge/discharge control circuit 9634 illustrated in FIG. 6B is described with reference to a block diagram in FIG. 6C. The solar cell 9633, the battery 9635, the DC-to-DC converter 9636, a converter 9637, switches SW1 to SW3, and the display portion 9631 are illustrated in FIG. 6C, and the battery 9635, the DC-to-DC converter 9636, the converter 9637, and the switches SW1 to SW3 correspond to the charge/discharge control circuit 9634 illustrated in FIG. 6B.

First, an example of the operation in the case where electric power is generated by the solar cell 9633 using external light is described. The voltage of electric power generated by the solar cell is raised or lowered by the DC-to-DC converter 9636 so that the electric power has a voltage for charging the battery 9635. Then, when the electric power from the solar cell 9633 is used for the operation of the display portion 9631, the switch SW1 is turned on and the voltage of the electric power is raised or lowered by the converter 9637 so as to be a voltage needed for the display portion 9631. In addition, when display on the display portion 9631 is not performed, the switch SW1 may be turned off and the switch SW2 may be turned on so that the battery 9635 is charged.

Note that the solar cell 9633 is described as an example of a power generation means; however, without limitation thereon, the battery 9635 may be charged using another power generation means such as a piezoelectric element or a thermoelectric conversion element (Peltier element). For example, the battery 9635 may be charged with a non-contact power transmission module which is capable of charging by transmitting and receiving power by wireless (without contact), or another charging means may be used in combination.

Figure 6C:
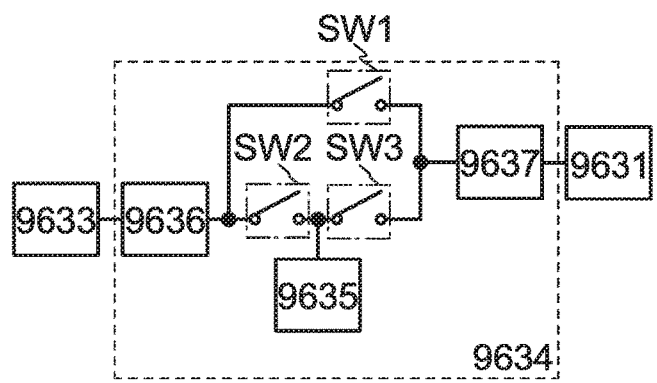

It is needless to say that one embodiment of the present invention is not limited to the electrical appliance illustrated in FIGS. 6A to 6C as long as the power storage device of one embodiment of the present invention is included.

This embodiment can be implemented in appropriate combination with any of the structures described in the other embodiments.

Embodiment 5

An example of a moving object driven by electric motors using electric power from the power storage device of one embodiment of the present invention is described with reference to FIGS. 7A and 7B.

The power storage device of one embodiment of the present invention can be used as a control battery. The control battery can be externally charged by electric power supply using plug-in systems or contactless power feeding. Note that in the case where the moving object is a train vehicle, the train vehicle can be charged by power supply from an overhead cable or a conductor rail.

Figure 7A:
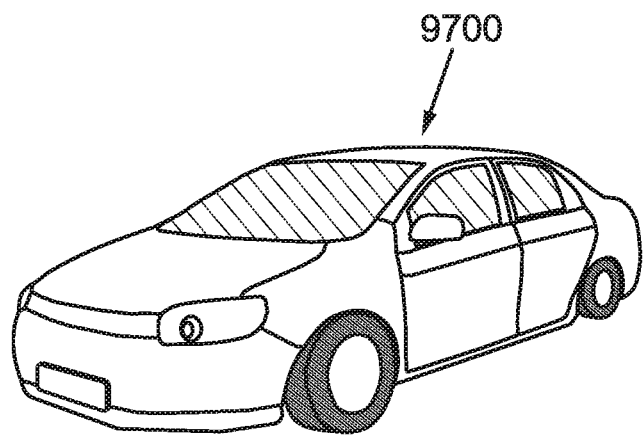
FIGS. 7A and 7B are diagrams illustrating an electrical device including a power storage device of one embodiment of the present invention.
Figure 7B:
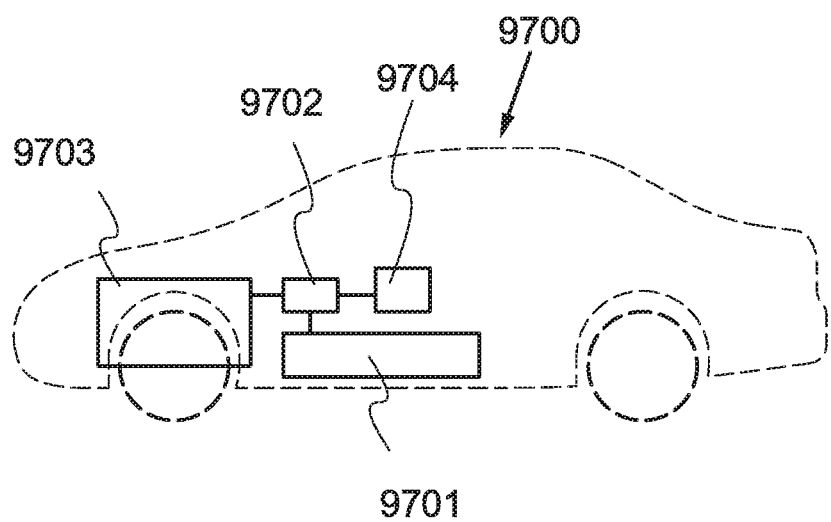

FIGS. 7A and 7B illustrate an example of an electric vehicle. An electric vehicle 9700 is equipped with a power storage device 9701. The output of the electric power of the power storage device 9701 is controlled by a control circuit 9702 and the electric power is supplied to a driving device 9703. The control circuit 9702 is controlled by a processing unit 9704 including a ROM, a RAM, a CPU, or the like which is not illustrated.

The driving device 9703 includes a DC motor or an AC motor either alone or in combination with an internal-combustion engine. The processing unit 9704 outputs a control signal to the control circuit 9702 on the basis of input data such as data on operation (e.g., acceleration, deceleration, or stop) by a driver of the electric vehicle 9700 or data on driving the electric vehicle 9700 (e.g., data on an upgrade or a downgrade, or data on a load on a driving wheel). The control circuit 9702 adjusts the electric energy supplied from the power storage device 9701 in accordance with the control signal of the processing unit 9704 to control the output of the driving device 9703. In the case where the AC motor is mounted, although not illustrated, an inverter which converts direct current into alternate current is also incorporated.

The power storage device 9701 can be externally charged by electric power supply using a plug-in system. For example, the power storage device 9701 is charged through a power plug from a commercial power supply. The power storage device 9701 can be charged by converting external power into DC constant voltage having a predetermined voltage level through a converter such as an AC-DC converter. When the power storage device of one embodiment of the present invention is provided as the power storage device 9701, a shorter charging time can be brought about and improved convenience can be realized. Moreover, the higher charging and discharging rate of the power storage device 9701 can contribute to greater acceleration and excellent performance of the electric vehicle 9700. When the power storage device 9701 itself can be more compact and more lightweight as a result of improved characteristics of the power storage device 9701, the vehicle can be lightweight and fuel efficiency can be increased.

This embodiment can be implemented in appropriate combination with any of the structures described in the other embodiments.

EXAMPLE 1

In this example, a description is given of the calculation result of the interaction between an alicyclic quaternary ammonium cation and an electron donating substituent in an ionic liquid included in the nonaqueous electrolyte of one embodiment of the present invention.

In this example, the lowest unoccupied molecular orbitals (LUMO levels) of nine kinds of alicyclic quaternary ammonium cations represented by Structural Formulae ($\alpha$-1) to ($\alpha$-9) were determined by the quantum chemical calculation. The nine kinds of alicyclic quaternary ammonium cations each include a methyl group as any of the substituents $R_1$ to $R_5$ in General Formula (G1). The results are shown in Table 1. In addition, as a comparative example, the lowest unoccupied molecular orbital (LUMO level) of an (N-methyl-N-propylpiperidinium) cation (see Structural Formula ($\alpha$-10)) that is a cation of an ionic liquid having a reduction potential substantially equivalent to an oxidation-reduction potential of lithium is also shown in Table 1.

[Chemical Formula 13]

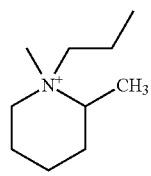
($\alpha$-1)

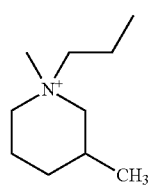
($\alpha$-2)

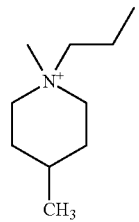
($\alpha$-3)

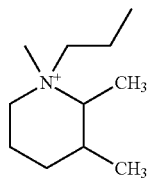
($\alpha$-4)

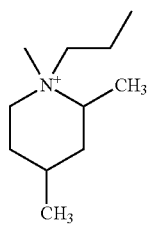
($\alpha$-5)

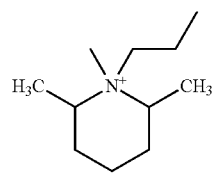
($\alpha$-6)

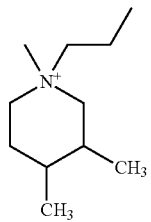
($\alpha$-7)

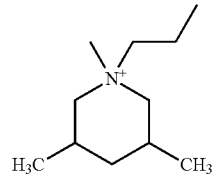
($\alpha$-8)

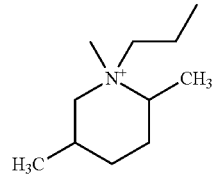
($\alpha$-9)

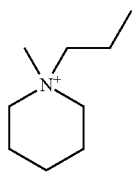
(α-10)

TABLE 1

| | LUMO Level |
|---|---|
| Structural Formula (α-1) | −3.047 [eV] |
| Structural Formula (α-2) | −3.174 [eV] |
| Structural Formula (α-3) | −3.192 [eV] |
| Structural Formula (α-4) | −2.941 [eV] |
| Structural Formula (α-5) | −3.013 [eV] |
| Structural Formula (α-6) | −2.877 [eV] |
| Structural Formula (α-7) | −3.125 [eV] |
| Structural Formula (α-8) | −3.102 [eV] |
| Structural Formula (α-9) | −2.970 [eV] |
| Structural Formula (α-10) | −3.244 [eV] |

In the quantum chemical calculation of this example, the optimal molecular structures in the ground state and a triplet state of the alicyclic quaternary ammonium cations represented by Structural Formulae (α-1) to (α-9) and the (N-methyl-N-propylpiperidinium) cation were calculated by using the density functional theory (DFT). In the DFT, the total energy is represented as the sum of potential energy, electrostatic energy between electrons, electronic kinetic energy, and exchange-correlation energy including all the complicated interactions between electrons. Also in the DFT, an exchange-correlation interaction is approximated by a functional (function of another function) of one electron potential represented in terms of electron density to enable highly accurate calculations. Here, B3LYP which was a hybrid functional was used to specify the weight of each parameter related to exchange-correlation energy. In addition, as a basis function, 6-311 (a basis function of a triple-split valence basis set using three contraction functions for each valence orbital) was applied to all the atoms. By the above basis function, for example, orbits of 1s to 3s are considered in the case of hydrogen atoms while orbits of 1s to 4s and 2p to 4p are considered in the case of carbon atoms. Furthermore, to improve calculation accuracy, the p function and the d function as polarization basis sets were added respectively to hydrogen atoms and atoms other than hydrogen atoms.

Note that Gaussian 09 was used as a quantum chemical calculation program. A high performance computer (manufactured by SGI Japan, Ltd., Altix 4700) was used for the calculations. The quantum chemical calculation was performed assuming that all of the alicyclic quaternary ammonium cations represented by Structural Formulae (α-1) to (α-10) had the most stable structure and were in a vacuum.

The reduction resistance of the cation can be measured relative to the reduction resistance of lithium by comparing the LUMO level of the cation with the LUMO level of the (N-methyl-N-propylpiperidinium) cation having the reduction potential substantially equivalent to the oxidation-reduction potential of lithium. That is, an ionic liquid including any of the alicyclic quaternary ammonium cations represented by Structural Formulae (α-1) to (α-9) each having the LUMO level higher than that of the (N-methyl-N-propylpiperidinium) cation has higher reduction resistance than lithium.

As shown in Table 1, the LUMO level of the (N-methyl-N-propylpiperidinium) cation that is the comparative example represented by Structural Formula (α-10) is −3.244 eV. The LUMO levels of the alicyclic quaternary ammonium cations represented by Structural Formulae (α-1) to (α-9) are all higher than −3.244 eV.

Consequently, the ionic liquid including any of the alicyclic quaternary ammonium cations represented by Structural Formulae (α-1) to (α-9) are considered to have higher reduction resistance than lithium that is a typical low potential negative electrode material. This is because an inductive effect caused by introducing the electron donating substituent into the alicyclic quaternary ammonium cation eased electric polarization of the alicyclic quaternary ammonium cation, so that the alicyclic quaternary ammonium cation was less likely to accept electrons.

Thus, the reduction potential of the ionic liquid including the alicyclic quaternary ammonium cation can be lowered by introducing the electron donating substituent into the alicyclic quaternary ammonium cation. Therefore, with the use of the ionic liquid with a low reduction potential as the nonaqueous electrolyte of one embodiment of the present invention, a power storage device with favorable cycle characteristics and high reliability can be manufactured.

Note that this example can be implemented in combination with any of the structures described in other embodiments and examples, as appropriate.

EXAMPLE 2

In this example, in a synthesis method of the ionic liquid of one embodiment of the present invention, the amount of a by-product included in the synthesized ionic liquid depending on the kind of a reaction solvent is described. Note that in this example, 1,3-dimethyl-1-propylpiperidinium bis(fluorosulfonyl)amide (abbreviation: 3mPP13-FSA) represented by Structural Formula (α-11) is described as an example.

[Chemical Formula 14]

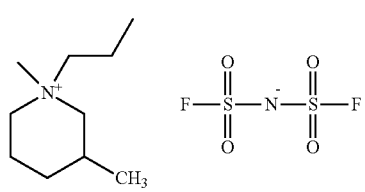
(α-11)

First, a synthesis method of 3mPP13-FSA which includes a by-product is described with reference to Synthesis Scheme (S-3).

[Chemical Formula 15]

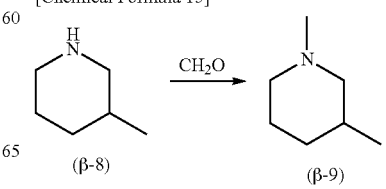
(S-3)

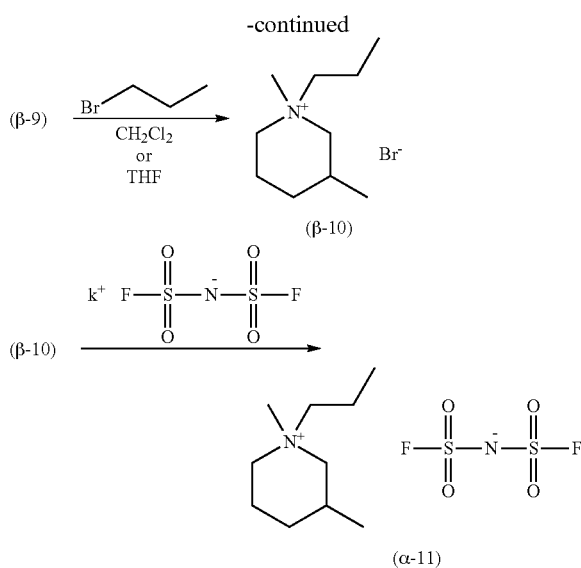

First, the reaction of synthesizing Structural Formula (β-9) from Structural Formula (β-8) is described. 3-Methylpiperidine (1.98 g, 200 mmol) was gradually added to formic acid (15.6 g, 300 mmol) while cooling with water. Next, formaldehyde (22.5 ml, 300 mmol) was added to this solution. This solution was heated to 100° C. and cooled back to room temperature after a bubble generation, and was stirred for about 30 minutes. Then, the solution was heated and refluxed for one hour.

The formic acid was neutralized with sodium carbonate, the solution was extracted with hexane and dried over magnesium sulfate, and the solvent was distilled off, whereby 1,3-dimethylpiperidine (12.82 g, 113 mmol) which was a light yellow liquid was obtained.

Next, the reaction of synthesizing Structural Formula (β-10) from Structural Formula (β-9) is described. Dichloromethane (10 ml) and bromopropane (20.85 g, 170 mmol) were added to the obtained light yellow liquid, and the obtained light yellow liquid was heated and refluxed for 24 hours, so that a white precipitate was generated. After filtration, the remaining substance was recrystallized with the use of a mixed solvent of ethanol and ethyl acetate and dried under reduced pressure at 80° C. for 24 hours, whereby 1,3-dimethyl-1-propylpiperidinium bromide (19.42 g, 82 mmol) which was a white solid was obtained.

Next, the reaction of synthesizing Structural Formula (α-11) from Structural Formula (β-10) is described. 1,3-Dimethyl-1-propylpiperidinium bromide (17.02 g, 72 mmol) and potassium bis(fluorosulfonyl)amide (17.04 g, 78 mmol) were mixed and stirred in pure water, so that an ionic liquid which is insoluble in water was obtained immediately. This ionic liquid was extracted with dichloromethane and then washed with pure water six times, and dried in vacuum at 60° C. through a trap at −80° C.; thus, an ionic liquid represented by Structural Formula (α-11), i.e., 3mPP13-FSA (20.62 g, 61 mmol) was obtained. Note that 3mPP13-FSA obtained by the above synthesis method is referred to as Synthetic Material A for convenience.

The measurement results of the electro spray ionization mass spectrometry (ESI-MS) of the obtained compound are shown below.

MS (ESI-MS): m/z=156.2 (M)$^+$; $C_{10}H_{22}N$ (156.2), 179.98 (M)$^-$; $F_2NO_4S_2$ (180.13)

The measurement result of the electro spray ionization mass spectrometry corresponded to 3mPP13-FSA.

Next, Synthetic Material A was identified by a nuclear magnetic resonance (NMR) method.

$^1$H NMR data of the obtained compound is shown below.

$^1$H-NMR(CDCl$_3$, 400M Hz, 298 K): δ (ppm) 1.02-1.09 (m, 6H), 1.21-1.26, 1.69-1.75 (m, 2H), 1.83-1.91 (m, 2H), 1.94-1.97 (m, 2H), 1.97-2.15 (m, 1H), 2.77-2.87, 3.30-3.43 (m, 2H), 3.05, 3.10 (s, 3H), 3.15-3.54 (m, 2H), 3.25-3.29 (m, 2H)

Figure 8A:
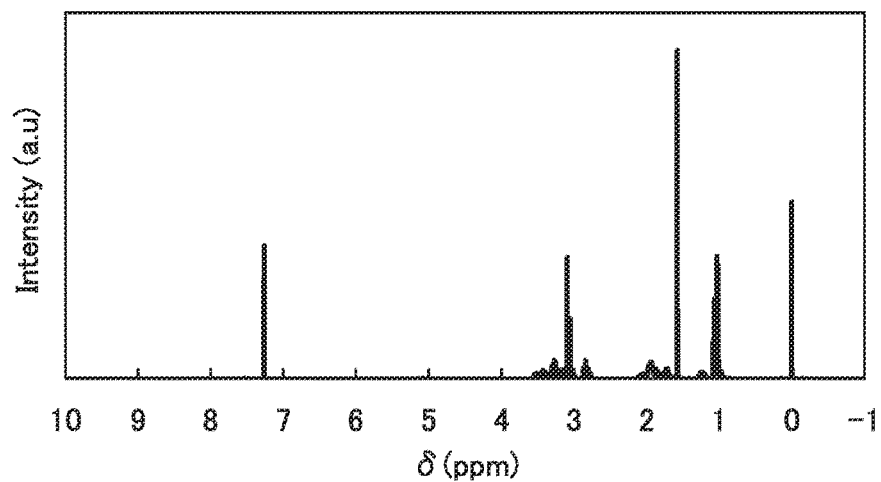
FIGS. 8A to 8C are $^1$H NMR charts of an ionic liquid of one embodiment of the present invention.
Figure 8B:
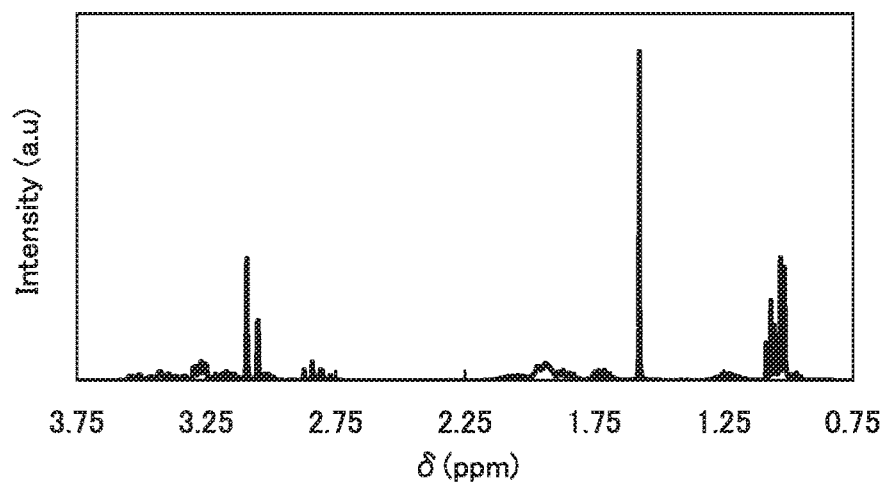
Figure 8C:
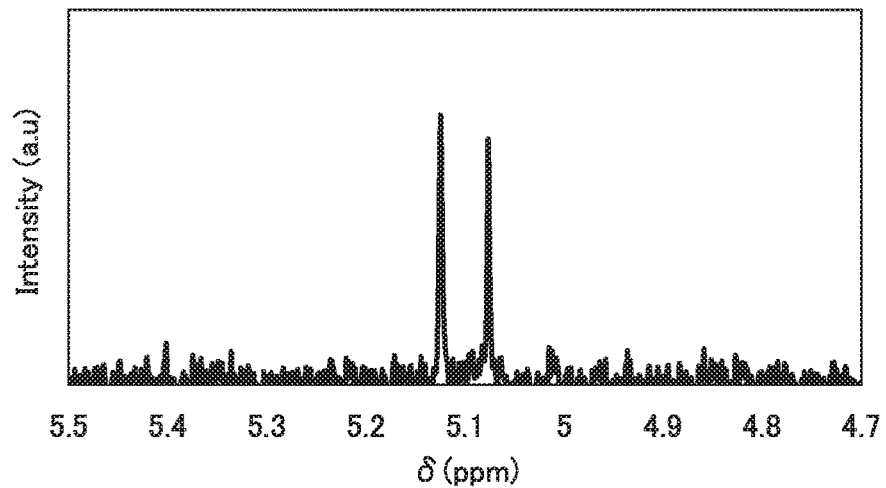

In addition, the $^1$H-NMR charts are shown in FIGS. 8A to 8C. Note that FIG. 8B is a chart showing an enlargement of FIG. 8A in the range of 0.750 ppm to 3.75 ppm. FIG. 8C is a chart showing an enlargement of FIG. 8A in the range of 4.70 ppm to 5.50 ppm.

The chart in FIG. 8B shows peaks corresponding to a proton of 3mPP13 that is a cation of the synthesized ionic liquid.

The chart in FIG. 8C shows peaks corresponding to a proton of a quaternary ammonium cation (by-product) represented by Structural Formula (α-12), which was obtained by the reaction of 1,3-dimethylpiperidine represented by Structural Formula (β-9) with dichloromethane used as the reaction solvent in the reaction for synthesizing Structural Formula (β-10) from Structural Formula (β-9) in Synthesis Scheme (S-3). Consequently, it was confirmed that 1-chloromethyl-1,3-dimethylpiperidinium bis(fluorosulfonyl)amide (by-product) represented by Structural Formula (α-12) was included in Synthetic Material A, in addition to 3mPP13-FSA that was the target substance.

[Chemical Formula 16]

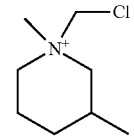

(α-12)

Next, a description is given of a case where tetrahydrofuran is used as the reaction solvent in the reaction of synthesizing Structural Formula (β-10) from Structural Formula (β-9) in Synthesis Scheme (S-3).

Steps up to and including the step of synthesizing Structural Formula (β-9) are the same as those in the case of Synthetic Material A. Tetrahydrofuran (10 ml) and bromopropane (20.85 g, 170 mmol) were added to the obtained light yellow liquid, and the obtained light yellow liquid was heated and refluxed for 24 hours, so that a white precipitate was generated. After filtration, the remaining substance was recrystallized with the use of a mixed solvent of ethanol and ethyl acetate and dried under reduced pressure at 80° C. for 24 hours, whereby 1,3-dimethyl-1-propylpiperidinium bromide (20.66 g, 87 mmol) which was a white solid was obtained.

In the reaction of synthesizing Structural Formula (α-11) from Structural Formula (β-10), 1,3-dimethyl-1-propylpiperidinium bromide (20.53 g, 87 mmol) and potassium bis(fluorosulfonyl)amide (20.96 g, 96 mmol) were prepared, and operations similar to those in the case of Synthetic Material A were conducted, whereby the ionic liquid represented by Structural Formula (α-11) (26.58 g, 79 mmol), i.e., 3mPP13-FSA, was obtained. Note that 3mPP13-FSA obtained by the above synthesis method is referred to as Synthetic Material B for convenience.

The measurement results of the electro spray ionization mass spectrometry (ESI-MS) of the obtained compound are shown below.

MS (ESI-MS): m/z=156.2 (M)$^+$; $C_{10}H_{22}N$ (156.2), 179.98 (M)$^-$; $F_2NO_4S_2$ (180.13)

Next, Synthetic Material B was identified by a nuclear magnetic resonance (NMR) method and mass spectrometry.

$^1$H NMR data of the obtained compound is shown below.

$^1$H-NMR(CDCl$_3$, 400 MHz, 298 K): δ (ppm) 0.96-1.08 (m, 6H), 1.18-1.27, 1.68-1.78 (m, 2H), 1.80-1.91 (m, 2H), 1.91-2.00 (m, 2H), 2.00-2.15 (m, 1H), 2.74-2.87, 3.30-3.45 (m, 2H), 3.05, 3.10 (s, 3H), 3.12-3.56 (m, 2H), 3.25-3.30 (m, 2H)

Figure 9A:
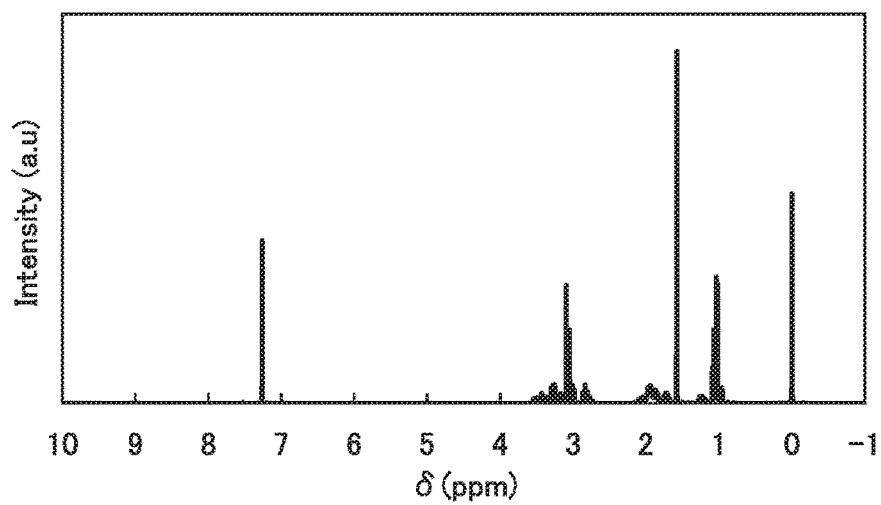
FIGS. 9A to 9C are $^1$H NMR charts of an ionic liquid of one embodiment of the present invention.
Figure 9B:
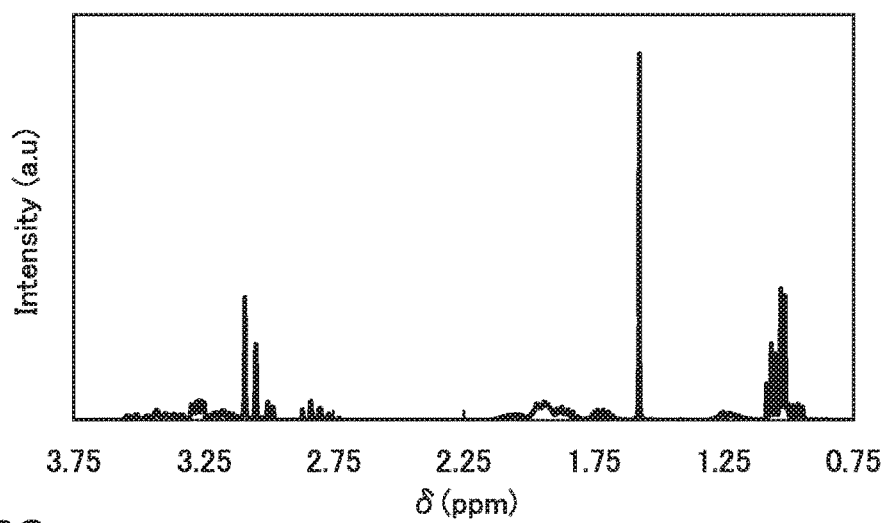
Figure 9C:
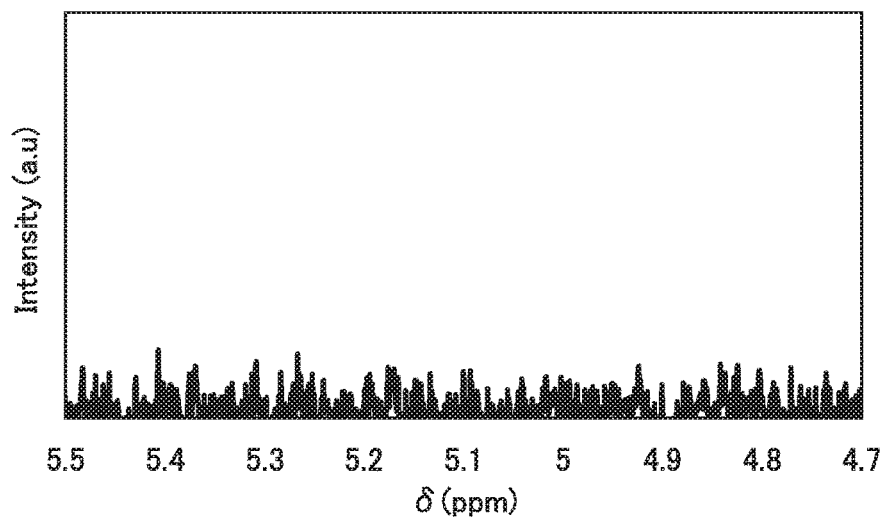

In addition, the $^1$H-NMR charts are shown in FIGS. 9A to 9C. Note that FIG. 9B is a chart showing an enlargement of FIG. 9A in the range of 0.750 ppm to 3.75 ppm. FIG. 9C is a chart showing an enlargement of FIG. 9A in the range of 4.70 ppm to 5.50 ppm.

The chart in FIG. 9B shows peaks corresponding to a proton of 3mPP13 that is a cation of the synthesized ionic liquid as in the case of Synthetic Material A.

Further, peaks corresponding to the proton of 1-chloromethyl-1,3-dimethylpiperidinium bis(fluorosulfonyl)amide (by-product) represented by Structural Formula (α-12), which were observed in Synthetic Material A, were not observed in the chart in FIG. 9C. For this reason, it was confirmed that Synthetic Material B was 3mPP13-FSA that was the target substance, and the 1-chloromethyl-1,3-dimethylpiperidinium bis(fluorosulfonyl)amide content was reduced to such an extent that peaks corresponding thereto were not detected (the lower limit of detection).

As described above, when the ionic liquid included in the nonaqueous electrolyte of one embodiment of the present invention is synthesized without the use of an organic solvent including a halogen element, a high-purity ionic liquid in which the by-product content is reduced can be provided. Further, with the use of the ionic liquid as a solvent for a nonaqueous electrolyte, a high-performance power storage device can be manufactured. Specifically, a power storage device having favorable cycle characteristics and high reliability even in an operating environment at relatively high temperature can be manufactured.

EXAMPLE 3

In this example, a description is given of the relation between the amount of a by-product included in an ionic liquid used as a solvent for a nonaqueous electrolyte and deterioration in characteristics of a power storage device due to the by-product.

The amount of the by-product included in the ionic liquid of the nonaqueous electrolyte of one embodiment of the present invention is described. Note that as in the case of Synthetic Material A in Example 2, it is difficult to directly weigh the amount of the by-product included in the produced ionic liquid, i.e., 3mPP13-FSA. For this reason, 1-chloromethyl-1,3-dimethylpiperidinium bis(fluorosulfonyl)amide identified as the by-product of the ionic liquid, i.e., 3mPP13-FSA described in Example 2 was synthesized and added to an ionic liquid in which a by-product was reduced as in the case of Synthetic Material B in Example 2 to obtain a sample, and the sample was used for indirect quantification of an upper limit of the amount of the by-product included in the ionic liquid.

Specifically, samples were obtained by adding 1-chloromethyl-1,3-dimethylpiperidinium bis(fluorosulfonyl)amide that was the by-product to Synthetic Material B in Example 2 at different concentrations, and the samples were measured by a linear sweep voltammogram, whereby the upper limit of the by-product content was quantified indirectly.

A synthesis method of 1-chloromethyl-1,3-dimethylpiperidinium bis(fluorosulfonyl)amide is described with reference to Synthesis Scheme (S-4).

[Chemical Formula 17]

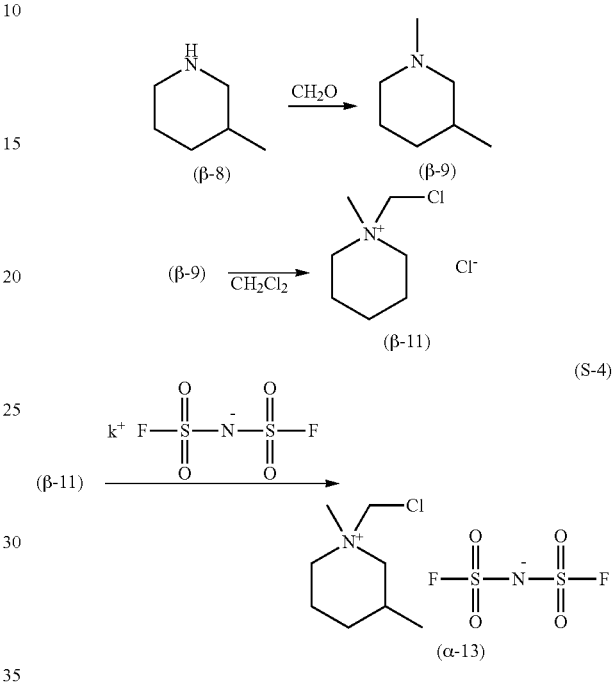

The reaction of synthesizing Structural Formula (β-9) from Structural Formula (β-8) in Synthesis Scheme (S-4) is described. 3-Methylpiperidine (1.98 g, 200 mmol) was gradually added to formic acid (15.6 g, 300 mmol) while cooling with water. Next, formaldehyde (22.5 ml, 300 mmol) was added to this solution. This solution was heated to 100° C. and cooled back to room temperature after a bubble generation, and was stirred for about 30 minutes. Then, the solution was heated and refluxed for one hour.

The formic acid was neutralized with sodium carbonate, the solution was extracted with hexane and dried over magnesium sulfate, and the solvent was distilled off, whereby 1,3-dimethylpiperidine (12.82 g, 113 mmol) which was a light yellow liquid was obtained.

Next, the reactions from Structural Formula (β-8) to Structural Formula (β-11) in Synthesis Scheme (S-4) are described. Dichloromethane (10 ml) was added to the obtained light yellow liquid, and the obtained light yellow liquid was heated and refluxed for 24 hours, so that a white precipitate was generated. After filtration, the remaining substance was recrystallized from ethanol and ethyl acetate and dried under reduced pressure at 80° C. for 24 hours, whereby 1-chloromethyl-1,3-dimethylpiperidinium chloride (2.75 g, 14 mmol) which was a white solid was obtained.

Next, the reactions from Structural Formula (β-11) to Structural Formula (α-13) in Synthesis Scheme (S-4) are described. 1-Chloromethyl-1,3-dimethylpiperidinium chloride (2.75 g, 14 mmol) and potassium bis(fluorosulfonyl) amide (3.35 g, 15 mmol) were mixed and stirred in pure water, so that an ionic liquid which is insoluble in water was obtained immediately. This ionic liquid was extracted with methylene chloride and then washed with pure water six times, and dried in vacuum at room temperature through a trap at −80° C.; thus, an ionic liquid (2.79 g, 8 mmol) that was 1-chloromethyl-1,3-dimethylpiperidinium bis(fluorosulfonyl)amide was obtained. Note that 1-chloromethyl-1, 3-dimethylpiperidinium bis(fluorosulfonyl)amide obtained by the above synthesis method is referred to as 3mPP11C1-FSA for convenience.

The measurement results of the electro spray ionization mass spectrometry (ESI-MS) of the obtained compound are shown below.

MS (ESI-MS): m/z=162.24 (M)$^+$; $C_8H_{17}NCl$ (162.68), 180.07 (M)$^-$; $F_2NO_4S_2$ (180.13)

Next, the obtained compound was identified by a nuclear magnetic resonance (NMR) method.

$^1$H NMR data of the obtained compound is shown below.
$^1$H-NMR(CDCl3,400 MHz,298K): δ (ppm) 0.99-1.10 (m,3H), 1.20-1.32, 1.85-1.95 (m,2H), 1.95-2.10 (m,2H), 2.10-2.20 (m,1H), 2.89-3.08, 3.30-3.42 (m,2H), 3.20, 3.23 (s,3H), 3.47-3.87 (m,2H), 5.09, 5.12 (s,2H)

Figure 10A:
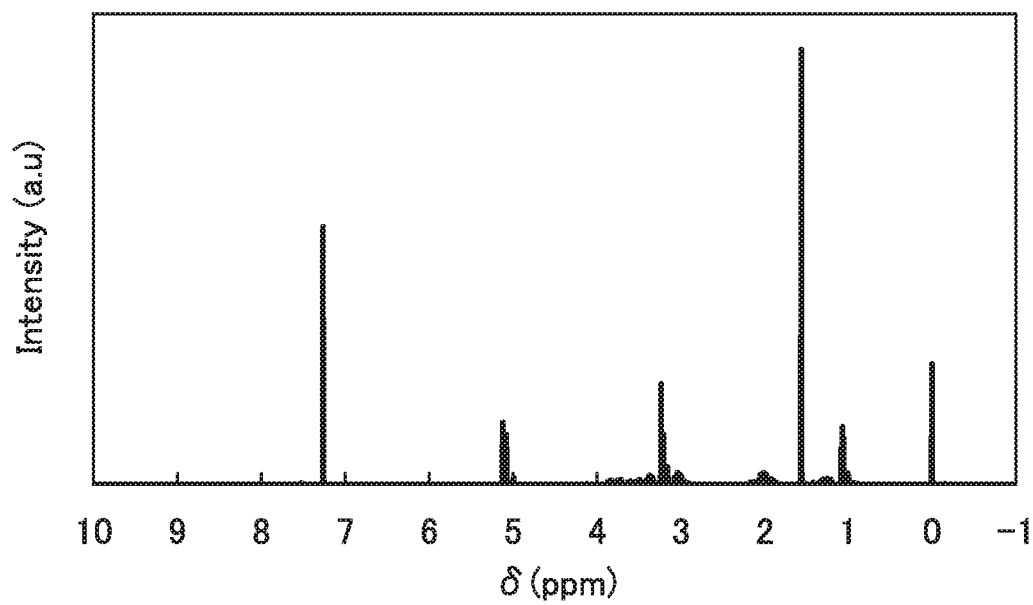
FIGS. 10A and 10B are $^1$H NMR charts of an ionic liquid of one embodiment of the present invention.
Figure 10B:
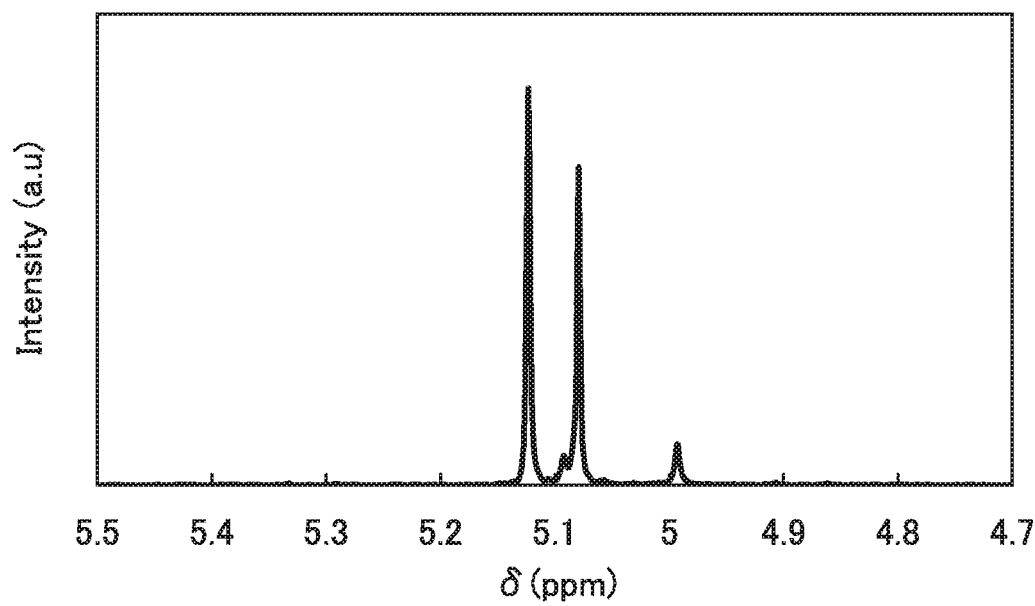

In addition, the $^1$H-NMR charts are shown in FIGS. 10A and 10B. Note that FIG. 10B is a chart showing an enlargement of FIG. 10A in the range of 4.70 ppm to 5.50 ppm.

The chart in FIG. 10B shows peaks corresponding to a proton of 3mPP11C1 that is a cation of 3mPP11C1-FSA.

The compound obtained in Synthesis Scheme (S-4) was confirmed to be 3mPP11C1-FSA that was the target substance.

Next, the synthesized 3mPP11C1-FSA was added to Synthetic Material B in Example 2 (3mPP13-FSA) to form samples. Sample A is a sample in which 0.089 g of 3mPP11C1-FSA and 1.02 g of Synthetic Material B were mixed (the amount of 3mPP11C1-FSA is 8.03 wt % per unit weight of Sample A). Sample B is a sample in which 0.014 g of 3mPP11C1-FSA and 1.01 g of Synthetic Material B were mixed (the amount of 3mPP11C1-FSA is 1.34 wt % per unit weight of Sample B). Sample C is a sample in which 0.0068 g of 3mPP11C1-FSA and 1.01 g of Synthetic Material B were mixed (the amount of 3mPP11C1-FSA is 0.67 wt % per unit weight of Sample C). Note that Sample D was formed of Synthetic Material A in Example 2 alone, and Sample E was formed of Synthetic Material B in Example 2 alone.

Samples A to E were measured by a linear sweep voltammogram.

The measurement was performed by using electrochemical measurement system HZ-5000 produced by HOKUTO DENKO CORPORATION in a glove box with an argon atmosphere. A glassy carbon electrode was used as a working electrode and a platinum wire was used for a counter electrode. A silver wire immersed in a solution in which silver trifluoromethanesulfonate was dissolved in 1-ethyl-3-methylimidazolium bis(trifluoromethanesulfonyl)amide at a concentration of 0.1 mol/L was used for a reference electrode. Oxidation-reduction potential of each Sample was corrected with reference to the oxidation-reduction potential of ferrocene (Fc/Fc$^+$). Note that a potential was scanned from spontaneous potential (vs. Fc/Fc$^+$) to −4 V (vs. Fc/Fc$^+$).

Figure 11:
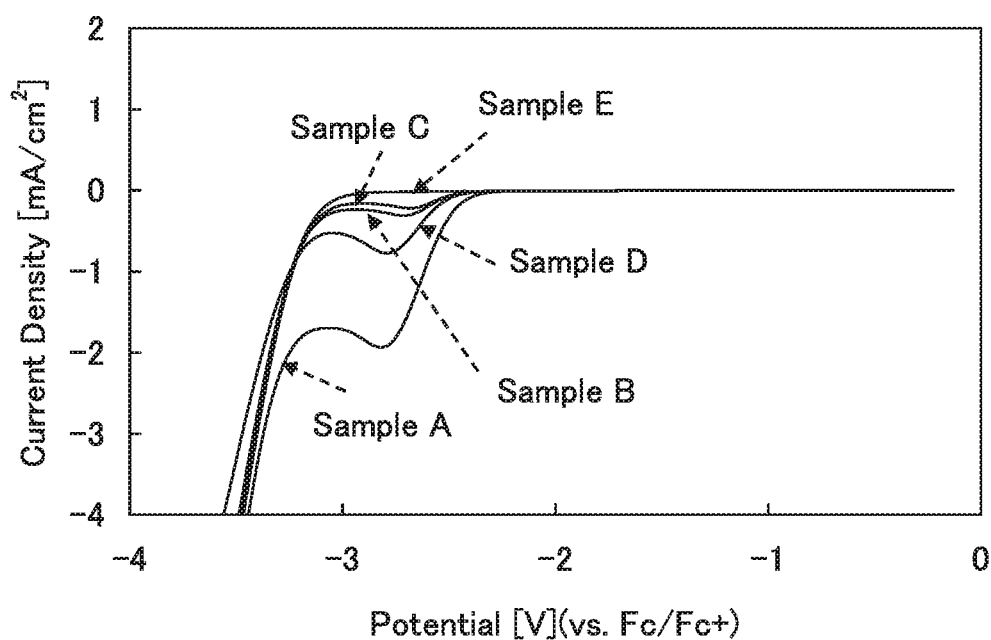
FIG. 11 is a graph showing current versus voltage characteristics of an ionic liquid of one embodiment of the present invention.

FIG. 11 shows the linear sweep voltammogram of each of Samples A to E. In FIG. 11, the horizontal axis represents the scanned potential (V) and the vertical axis represents current density (mA/cm$^2$). Note that the reduction potential of each Sample was a potential at which a current density of −1 mA/cm$^2$ was detected while the potential was scanned.

FIG. 11 confirms that in each of Samples A to E, a peak of the reduction potential around −2.7 V to −2.8 V became large as the 3mPP11C1-FSA content increased. The peak of the reduction potential was not observed in the linear sweep voltammogram of Sample E in which the 3mPP11C1-FSA content was reduced to such an extent that the peaks corresponding to the proton of 3mPP11C1-FSA were not detected (the lower limit of detection) by NMR measurement. Therefore, the peak of the reduction potential can be said to be a peak corresponding to the reductive decomposition of 3mPP11C1-FSA.

Further, it was confirmed that in the ionic liquid synthesized with the use of an organic solvent including a halogen element (specifically, Synthetic Material A in Example 2), such as Sample D, a salt including 3mPP11C1 that was a cation of the by-product was unintentionally included at least at more than 1 wt %.

Here, another measurement was performed with a charged aerosol detector in order to confirm that the salt included 3mPP11C1 that was the cation of the by-product was unintentionally including at least at more than 1 wt % in the ionic liquid synthesized with the use of the organic solvent including the halogen element (specifically, Synthetic Material A in Example 2), such as Sample D.

The charged aerosol detector is a detector for high performance liquid chromatography which can detect an impurity included in the synthesized ionic liquid. Note that a column which can separate an ionic compound (specifically, Acclaim Trinity P1, 3 μm 3.0 mm×100 mm produced by Nippon Dionex K.K) was used for the high performance liquid chromatography in this example. Further, a peak area (or peak intensity) detected by the charged aerosol detector is increased as the weight of the compound to be detected increases.

Then, the calibration curve of the concentration of the salt including 3mPP11C1 to the solvent and a peak area to the concentration was constructed to calculate the concentration of the salt including 3mPP11C1 which is included in Sample D (i.e., Synthetic Material A in Example 2).

First, to construct the calibration curve, a solution in which 3mPP11C1-FSA synthesized in Synthesis Scheme (S-4) was mixed to acetonitrile was added to the charged aerosol detector, so that the peak area to the concentration of 3mPP11C1-FSA was examined. Note that six solutions were prepared with different 3mPP11C1-FSA concentrations in the following conditions: in Condition 1, the concentration was 0 μg/g; in Condition 2, 4 μg/g; in Condition 3, 13 μg/g; in Condition 4, 27 μg/g; in Condition 5, 56 μg/g; and in Condition 6, 100 μg/g. Note that the concentrations in Conditions 1 to 6 are each the proportion of 3mPP11C1FSA in the solution in which 3mPP11C1-FSA and acetonitrile were mixed.

Figure 14:
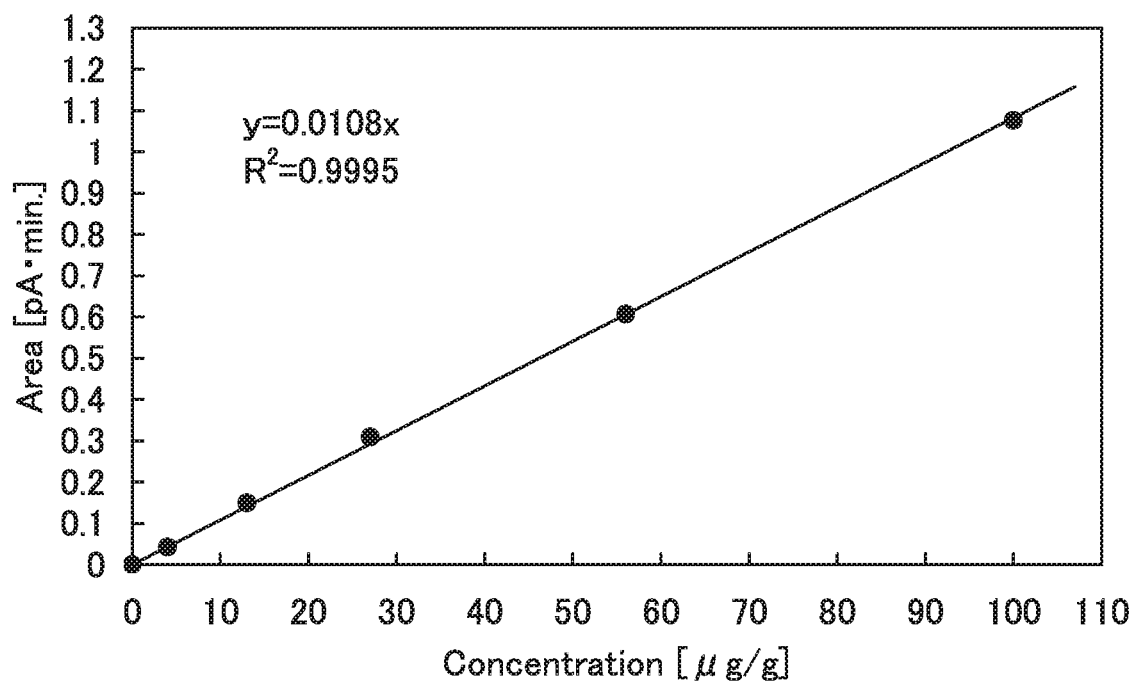
FIG. 14 is a graph showing a calibration curve for quantification of a by-product included in an ionic liquid synthesized with the use of an organic solvent including a halogen element.

The solutions in Conditions 1 to 6 were analyzed with the charged aerosol detector, and peaks obtained in Conditions 1 to 6 were calculated. The relation between the concentration of 3mPP11C1-FSA and the peak area is shown in a graph (calibration curve) in FIG. 14. Note that the calibration curve was constructed by linear approximation of the peak areas in Conditions 1 to 6. The formula of the calibration curve is y=0.0108x and a coefficient value of determination $R^2$ is 0.9995.

Next, a solution in which Sample D (Synthetic Material A in Example 2) and acetonitrile were mixed so that the proportion of Sample D in the solution is 999.1 μg/g was analyzed with the charged aerosol detector. A peak area to the concentration of 3mPP11C1-FSA in the solution was 0.11 pA·min. From the calibration curve in FIG. 14, the concentration of 3mPP11C1-FSA to the peak area was confirmed to be 10.2 μg/g, which was 1.02 wt % when converted into percentage by weight. Consequently, it was confirmed that in the ionic liquid synthesized with the use of the organic solvent including the halogen element (specifically, Synthetic Material A in Example 2), such as Sample D, the salt including 3mPP11C1 that was a cation of the by-product was unintentionally included at least at 1 wt % or more.

Next, cycle characteristics of a power storage device using the ionic liquid, i.e., 3mPP13-FSA as a solvent for a nonaqueous electrolyte were measured. Note that a coin-type lithium secondary battery was used as the power storage device. As the coin-type lithium secondary battery in this example, a lithium iron phosphate-graphite full cell, in which lithium iron phosphate ($LiFePO_4$) was used for one electrode and graphite was used for the other electrode, was manufactured.

A method for manufacturing the lithium iron phosphate-graphite full cell is described with reference to FIG. 12.

The full cell manufactured includes a housing 171 and a housing 172 which serve as external terminals, a positive electrode 148, a negative electrode 149, a ring-shaped insulator 173, a separator 156, a spacer 181, and a washer 183.

In the positive electrode 148, the positive electrode active material layer 143 containing a positive electrode active material, a conductive additive, and a binder at a weight ratio of 85:8:7 is provided over the positive electrode current collector 142 made of aluminum foil (15.958φ). Note that lithium iron phosphate (22.7 mg) was used as the positive electrode active material.

In the negative electrode 149, a negative electrode active material layer 146 containing a negative electrode active material, a conductive additive, and a binder at a weight ratio of 85:15:7.5 is provided over a negative electrode current collector 145 made of aluminum foil (16.156φ). Note that graphite (TSG-A1, produced by JFE Chemical Corporation, 10.7 mg) was used as the negative electrode active material.

For the separator 156, GF/C which is a glass fiber filter produced by Whatman Ltd. was used.

The positive electrode 148 was soaked in the nonaqueous electrolyte of one embodiment of the present invention for one hour. Note that in the nonaqueous electrolyte, lithium bis(trifluoromethanesulfonyl)amide (LiTFSA) was dissolved at a concentration of 1.0 mol/L in the ionic liquid that was Sample E (specifically Synthetic Material B described in Example 2), i.e., 3mPP13-FSA.

The housing 171 and the housing 172 were formed of stainless steel (SUS). The spacer 181 and the washer 183 were also formed of stainless steel (SUS).

Figure 12:
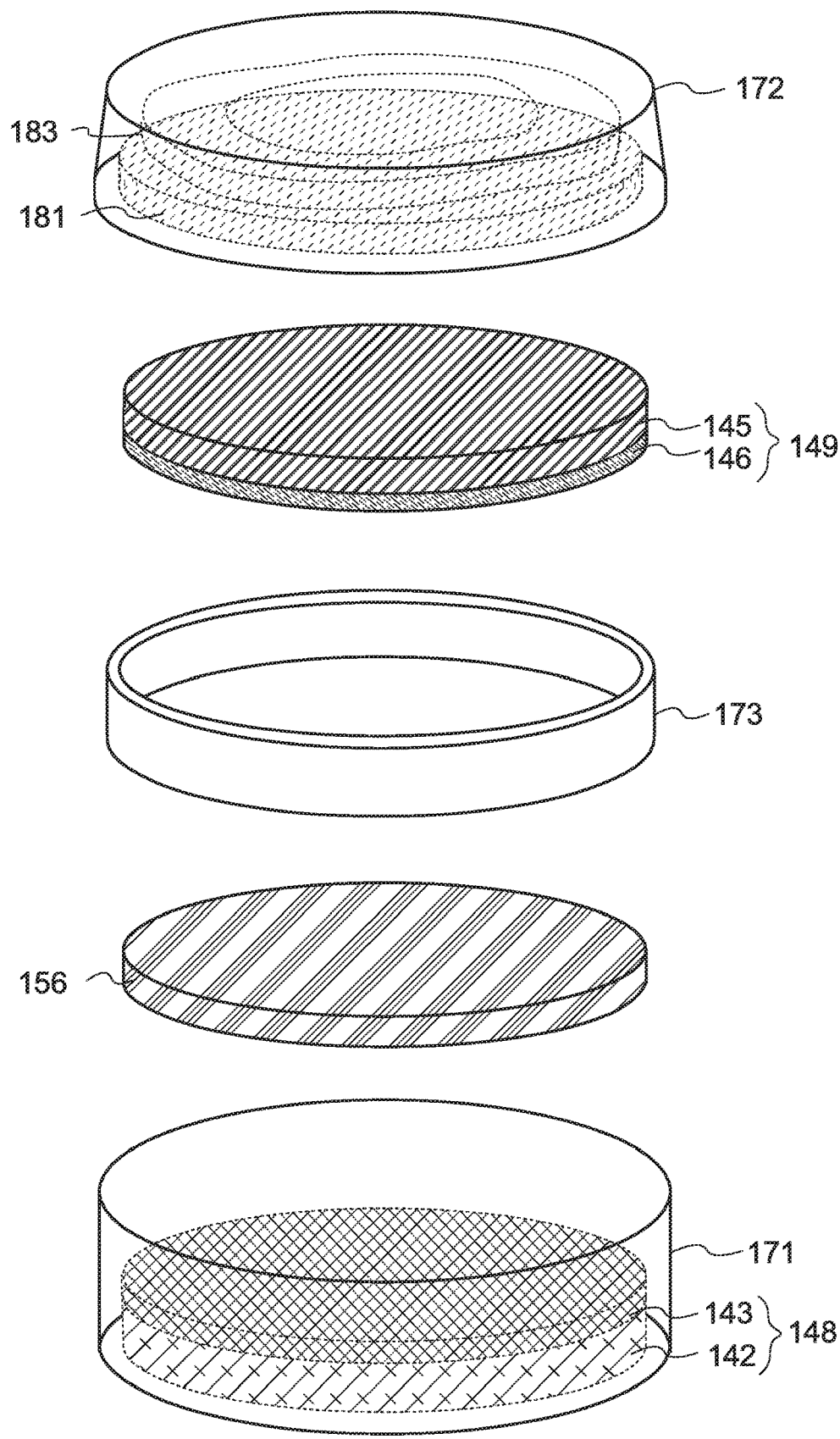
FIG. 12 is a diagram illustrating a method for manufacturing a power storage device of one embodiment of the present invention.

As illustrated in FIG. 12, the housing 171, the positive electrode 148, the separator 156, the ring-shaped insulator 173, the negative electrode 149, the spacer 181, and the housing 172 were stacked in this order from the bottom side. The positive electrode 148, the negative electrode 149 and the separator 156 were soaked in the non-aqueous electrolyte. Then, the housing 171 and the housing 172 were crimped to each other with a "coin cell crimper." Thus, the lithium iron phosphate-graphite full cell was manufactured.

In the manufactured full cells, the full cell using Sample E is referred to as Full Cell 1. As a comparative example, a coin-type lithium secondary battery using a nonaqueous electrolyte obtained by dissolving LiTFSA in the ionic liquid that was Sample D, i.e., 3mPP13-FSA, at a concentration of 1.0 mol/L is referred to as Full Cell 2.

Next, the cycle characteristics of Full Cells 1 and 2 were measured. The measurement was performed with a charge-discharge measuring instrument (produced by TOYO SYSTEM Co., LTD) in a constant temperature bath at 60° C. Further, a constant-current mode was employed for the charging method of the measurement, and Full Cells 1 and 2 were charged at a constant current at a rate of approximately 0.1 C (0.19 mA/cm$^2$), and then discharged at the same C rate. Note that in the measurement, one cycle includes one charging and one discharging, and 80 cycles were performed.

Figure 13:
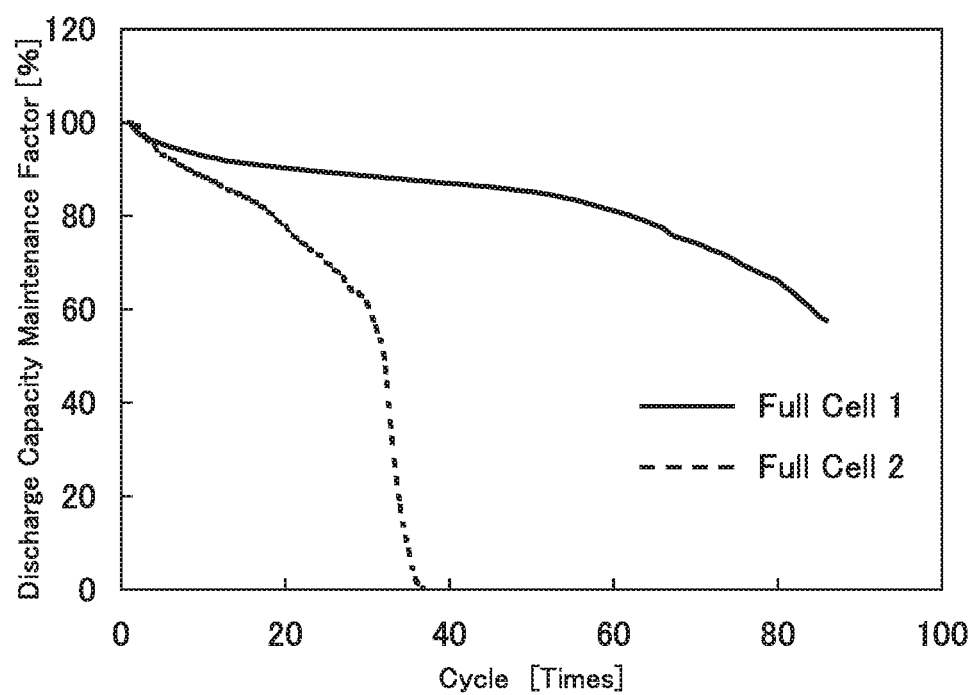
FIG. 13 is a graph showing cycle characteristics of a power storage device of one embodiment of the present invention.

The results of the cycle characteristics of Full Cells 1 and 2 are shown in FIG. 13. In FIG. 13, the horizontal axis represents the number of cycles of charging and discharging [times] and the vertical axis represents the discharge capacity maintenance factor [%] of Full Cells 1 and 2. Note that the capacity maintenance factor refers to the percentage of capacity after a certain number of cycles in the highest capacity during 80 cycles. In addition, in FIG. 13, a solid line shows the cycle characteristic of Full Cell 1 and a dashed line shows the cycle characteristic of Full Cell 2. From FIG. 13, the capacity maintenance factor of Full Cell 1 using Sample E as the solvent for the nonaqueous electrolyte was better than that of Full Cell 2 using Sample D as the solvent for the nonaqueous electrolyte.

Note that in view of Sample E including reduced amount of 3mPP11C1-FSA (by-product), Sample D including 3mPP11C1-FSA (by-product) whose amount is at least more than 1 wt % per unit weight of the solvent, and the results of the linear sweep voltammogram, the discharge capacity maintenance factor of Full Cell 2 was markedly decreased probably because the nonaqueous electrolyte was decomposed due to the decomposition of the by-product caused by repeated charging and discharging. Thus, with the use of the ionic liquid including the by-product whose amount is less than or equal to 1 wt % per unit weight of the ionic liquid, the cycle characteristics of the power storage device can be improved in an operating environment at relatively high temperature.

As described above, by using the ionic liquid in which the by-product content is reduced as the solvent for the non-aqueous electrolyte, deterioration in the characteristics caused by the decomposition of the by-product can be suppressed, and the power storage device can have high reliability in the operating environment at relatively high temperature.

This application is based on Japanese Patent Application serial No. 2011-282486 filed with Japan Patent Office on Dec. 23, 2011, the entire contents of which are hereby incorporated by reference.

What is claimed is:

1. A method of synthesizing an ionic liquid, comprising the steps of:
   reacting a tertiary amine compound and an alkyl halide compound in a first solution to obtain a first product; and
   exchanging an ion between the first product and a metal salt to obtain the ionic liquid,
   wherein the first solution comprises a first organic solvent which does not include a halogen element in the structural formula,
   wherein the tertiary amine compound comprises a six membered ring, wherein the first product comprises a cation represented by Formula (G1):

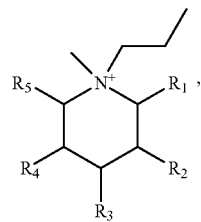
(G1)

wherein $R_1$ to $R_5$ each represent any one of a hydrogen atom, an alkyl group having 1 to 4 carbon atoms, a methoxy group, a methoxymethyl group and a methoxyethyl group, wherein a concentration of a compound represented by Formula (G2) in the ionic liquid is lower than 0.67 wt %:

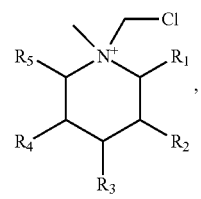
(G2)

and
wherein reacting the tertiary amine compound and the alkyl halide compound is performed under reflux.

2. The method according to claim 1, further comprising the step of:
reacting an amine compound and a carbonyl compound in a second solution to obtain the tertiary amine compound.

3. The method according to claim 2, wherein the second solution comprises a hydride.

4. The method according to claim 2, wherein the second solution comprises formic acid.

5. The method according to claim 1, wherein the alkyl halide compound is a propane halide.

6. The method according to claim 1, wherein the alkyl halide compound is bromopropane.

7. The method according to claim 1, wherein the metal salt comprises an anion selected from any of a monovalent imide-based anion, a monovalent methide-based anion, a perfluoroalkyl sulfonic acid anion, tetrafluoroborate and hexafluorophosphate.

8. The method according to claim 7, wherein the metal salt comprises potassium.

9. The method according to claim 8, wherein the ionic liquid comprises an alicyclic quaternary ammonium cation.

10. The method according to claim 1, wherein the first organic solvent is tetrahydrofuran.

11. The method according to claim 1, wherein the ionic liquid is obtained by distilling off the first organic solvent.

12. A method of synthesizing an ionic liquid, comprising the step of:
reacting a tertiary amine compound and an alkyl halide compound in a first solution to obtain a first product; and wherein the first solution comprises a first organic solvent which does not include a halogen element in the structural formula, wherein the first product comprises a cation represented by Formula (G1):

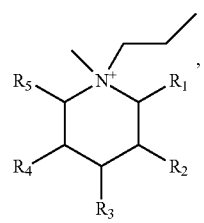
(G1)

wherein $R_1$ to $R_5$ each represent a hydrogen atom, an alkyl group having 1 to 4 carbon atoms, a methoxy group, a methoxymethyl group and a methoxyethyl group, wherein a concentration of a compound represented by Formula (G2) in the ionic liquid is lower than 0.67 wt %:

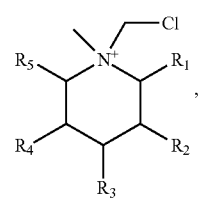
(G2)

and
wherein reacting the tertiary amine compound and the alkyl halide compound is performed under reflux.

13. The method according to claim 12,
wherein the tertiary amine compound is represented by Formula (13-2):

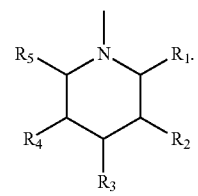
(β-2)

14. The method according to claim 13,
wherein the tertiary amine compound is represented by Formula (β-9):

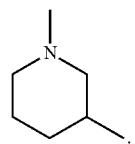
(β-9)

15. The method according to claim 12, further comprising the step of:
exchanging an ion between the first product and a metal salt to obtain the ionic liquid.

16. The method according to claim 15, wherein the ionic liquid comprises a cation represented by Formula (G1) and an anion selected from the group consisting of a monovalent imide-based anion, a monovalent methide-based anion, a perfluoroalkyl sulfonic acid anion, tetrafluoroborate, and hexafluorophosphate.

17. The method according to claim 12, wherein the first organic solvent is one of tetrahydrofuran and toluene.

18. A method of synthesizing an ionic liquid, comprising the step of:
reacting a tertiary amine compound and an alkyl halide compound in a first solution to obtain a first product; and
wherein the first solution comprises a first organic solvent which does not include a halogen element in the structural formula,
wherein the first product comprises a cation represented by Formula (G7):

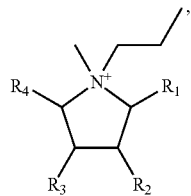

(G7)

wherein $R_1$ to $R_4$ each represent a hydrogen atom, an alkyl group having 1 to 4 carbon atoms, a methoxy group, a methoxymethyl group and a methoxyethyl group,
wherein a concentration of a compound represented by Formula (G8) in the ionic liquid is lower than 0.67 wt %:

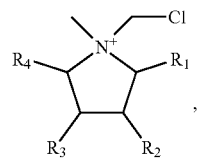

(G8)

and
wherein reacting the tertiary amine compound and the alkyl halide compound is performed under reflux.

19. The method according to claim 18, wherein the tertiary amine compound is represented by Formula (β-6):

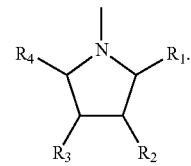

(β-6)

20. The method according to claim 18, further comprising the step of:
exchanging an ion between the first product and a metal salt to obtain the ionic liquid.

21. The method according to claim 20, wherein the ionic liquid comprises a cation represented by Formula (G7) and an anion selected from the group consisting of a monovalent imide-based anion, a monovalent methide-based anion, a perfluoroalkyl sulfonic acid anion, tetrafluoroborate, and hexafluorophosphate.

22. The method according to claim 18, wherein the first organic solvent is tetrahydrofuran.

* * * * *